(12) United States Patent
Brown et al.

(10) Patent No.: US 8,354,564 B2
(45) Date of Patent: Jan. 15, 2013

(54) PRODUCTION OF DRY ALCOHOL

(75) Inventors: Christopher J. Brown, Amherst, NY (US); Marian Simo, Tonawanda, NY (US); Vladimir Hlavacek, Clarence, NY (US)

(73) Assignee: BHS Technology LLC, Buffalo, NY (US)

( * ) Notice: Subject to any disclaimer, the term of this patent is extended or adjusted under 35 U.S.C. 154(b) by 1611 days.

(21) Appl. No.: 11/697,054

(22) Filed: Apr. 5, 2007

(65) Prior Publication Data

US 2007/0238906 A1    Oct. 11, 2007

Related U.S. Application Data

(60) Provisional application No. 60/744,430, filed on Apr. 7, 2006.

(51) Int. Cl.
| C07C 28/88 | (2006.01) |
| C07C 27/00 | (2006.01) |
| B01J 23/02 | (2006.01) |
| C01B 3/12  | (2006.01) |

(52) U.S. Cl. .......... 568/913; 518/712; 518/713; 502/84; 502/342; 502/343; 502/345; 423/655; 423/656; 435/162; 435/165; 435/160; 435/161; 122/32; 122/488; 122/489

(58) Field of Classification Search .................. 568/913; 518/712, 713; 502/84, 342, 343, 345; 435/160, 435/161, 162, 165; 423/655, 656; 165/134 R; 122/32, 488, 489; 44/53, 56
See application file for complete search history.

(56) References Cited

U.S. PATENT DOCUMENTS

| 2,579,601 | A | 12/1951 | Nelson et al. |
| 4,369,255 | A | 1/1983 | Supp |
| 4,517,298 | A | 5/1985 | Tedder |
| 4,539,076 | A | 9/1985 | Swain |
| 4,721,611 | A * | 1/1988 | Pinto et al. ..................... 423/655 |
| 4,869,067 | A | 9/1989 | Sears |
| 6,693,057 | B1 | 2/2004 | Cai et al. |
| 2004/0137288 | A1* | 7/2004 | Morgenstern .................. 429/17 |
| 2005/0107651 | A1 | 5/2005 | Sher et al. |

FOREIGN PATENT DOCUMENTS

WO    2005021474    3/2005

OTHER PUBLICATIONS

Lazier et al, The formation of carbon dioxide from alcohols, J. Phys. Chem., 1926, 30 (7), pp. 895-898.*

* cited by examiner

*Primary Examiner* — Thuan D Dang
(74) *Attorney, Agent, or Firm* — Paul T. Lavoie, Esq.

(57) ABSTRACT

A process for producing dry alcohol (including ethanol) that comprises at least one stage wherein a gaseous feedstock, which includes alcohol and water, is contacted with carbon monoxide in the presence of a water-gas shift catalyst, at a temperature sufficiently high so that carbon monoxide and water are consumed and carbon dioxide and hydrogen are produced, thereby removing a portion of the water. The process may include multiple stages; the dry alcohol produced contains 99.5 wt. % or greater of alcohol and 0.5 wt. % or less of water.

37 Claims, 13 Drawing Sheets

PRODUCTION OF DRY ALCOHOL

CROSS REFERENCE TO RELATED APPLICATIONS

This application claims the benefit of Provisional Patent Application No. 60/744,430, which was filed Apr. 7, 2006.

FIELD OF THE INVENTION

The present invention is directed to the purification of alcohol and, more particularly, to a process and an apparatus for the removal of water from mixtures of alcohol and water and the production of dry alcohol with simultaneous generation of energy. In certain cases, dry alcohol can be used as a fuel additive, and this energy efficient process further reduces reliance on fossil fuels.

BACKGROUND OF THE INVENTION

Decreasing world reserves and diminishing availability of crude oil have created considerable incentive for the development and use of alternative fuels. In recent years, the ever increasing value of fossil hydrocarbon liquids and gases has directed research and development to the possibilities of employing bio-mass materials for fuel purposes. In particular, attention has been focused on fermentation derived ethanol for car fuel purposes. Ethanol is gaining wide popularity as such a fuel. Ethanol can be combined with gasoline to form a mixture known as gasohol. Automobiles can run on gasohol containing up to about 20 volume percent ethanol without requiring engine modifications. To prevent phase separation during storage, gasohol should be essentially free of water. Therefore ethanol used for gasohol production is preferably at least 199 proof.

Ethanol is derived primarily from the fermentation of mash, usually from corn, grains, and/or sugar cane. During alcoholic fermentation, sugar, particularly glucose, is converted into ethanol and carbon dioxide in the presence of yeast cells that contain the enzyme complex zymase. Glucose is produced by enzymatic splitting of maltose, which is itself formed during the hydrolytic, enzymatic splitting of starch or is developed during the manufacture of sugar. In addition to ethanol, the ethanol solutions developed during alcoholic fermentation contain soluble and insoluble components of vegetable cells and builders, yeast cells, starch and fractions of starch, various sugars, salts and water. The ethanol content of the solutions obtained during alcoholic fermentation is usually about 12 wt. %, since a higher ethanol concentration becomes toxic to yeast and larger amounts of other metabolic chemicals are formed. At higher alcohol levels, the yeast die and fermentation ceases.

As described in the online *Encyclopaedia Brittanica*, rectification is the process of purifying alcohol by repeatedly or fractionally distilling it to remove water and undesirable compounds. A fermentation mixture primarily contains water, ethanol, solids, and yeast. Distillation involves increasing the percentage of ethanol in the mixture. The fermentation mixture furthermore contains small quantities of constituents such as, for example, organic aldehydes, acids, esters, and higher alcohols. The ones that remain in the product are called congeners, and the congener level is controlled by the particular rectification system and by the system's method of operation.

A multicolumn rectifying system commonly consisting of three to five columns had been used in earlier years. The first column is a preliminary separation column called the beer still, or analyzer. It usually consists of a series of metal plates with holes punched in them and baffles to control the liquid levels on the plates. The product coming from this column is generally between 55 and 80 percent ethanol. A 95-percent product can be produced on a two-column system consisting of a beer column and a rectifying column with further purification added in the additional columns.

Water cannot be completely removed from ethanol by distillation because of the formation of an azeotrope containing 95.5 wt. % ethanol and 4.5 wt. % water, which limits the upper concentration of ethanol that can be obtained by rectification regardless of the number of theoretical plates employed. Distillation processes have the further drawback that they require a large amount of energy. Special techniques are required to dehydrate ethanol beyond the 95.5 wt. % ethanol content level and typically require a considerable additional amount of energy. The high energy cost of ethanol separation by distillation is an economic impediment for using ethanol produced by alcoholic fermentation as an engine fuel.

Alcohols other than ethanol are also being considered for bio-fuel applications. For example, 1-butanol can be obtained by a fermentation process and used for this purpose. Thus, useful means of separating alcohols such as 1-butanol from water are also desirable.

Azeotropic or extraction distillation based separation processes are based on the addition of an entrainer to the ethanol-water system. Traditionally, distillation with a third component has been used to form a minimum azeotrope. This technique lowers the boiling point below 78.15° C., the boiling point of the ethanol-water azeotrope. This can be a binary azeotrope such as water-ethyl ether, reported by Othmer & Wentworth, *Ind. & Engr. Chem.*, 32, 1588 (1940), or a ternary azeotrope such as benzene-water-ethanol, well described in Kirk & Othmer, *Encyclopedia of Chemical Technology*. While the benzene-water-ethanol ternary is probably the most widely used method of dehydrating ethanol, it require the expenditure of a great deal of heat energy.

Extractive distillation involves the distillation of ethanol-water mixtures in the presence of an added solvent. The ethanol-water mixture is fed to a tray located in the intermediate part of the column, and the solvent is fed to a higher tray. The distillate contains water, with reduced amounts of ethanol; the bottom product contains solvent and ethanol with minimal amount of water. Subsequent distillation of the bottom product produces a second overhead with high concentration of ethanol. Both distillation steps may be conducted at atmospheric pressure, but it is preferred to operate the second distillation step below atmospheric pressure, for example, between 1 and 50 kPa.

Extractive distillation to remove water from ethanol is described in U.S. Pat. No. 1,469,447, where glycerin is used as the extractive agent; U.S. Pat. No. 2,559,519, where ethoxyethanol and butoxyethanol are employed; and U.S. Pat. No. 2,591,672, which discloses gasoline as being effective. Also, French Patent No. 1,020,351 describes the use of glycols, glycol ethers or glycol esters as extractive agents, and U.S. Pat. No. 2,591,671 reports the use of butyl, amyl and hexyl alcohols for this purpose. U.S. Pat. No. 2,901,404 suggests sulfuric acid, acetone or furfural as extractive distillation agents, and U.S. Pat. No. 4,349,416 teaches the use of ethylene glycol. U.S. Pat. No. 4,366,032 discloses ethanolamine and N-methyl pyrrolidone as effective extraction agents, and U.S. Pat. No. 4,400,241 reports the use of alkali-metal or alkaline-earth metal salts, sodium tetraborate dissolved in ethylene glycol, and dipotassium phosphate dissolved in glycerol. U.S. Pat. Nos. 4,428,798 and 4,455,198 propose the use of 2-phenyl phenol, cumyl phenol, diisopropyl phenol, cyclohexyl cyclohexanone, phenyl cyclohexanone, and cyclohexyl cyclohexanol as extraction agents. The disclosures of all of these patents are incorporated herein by reference.

Design and economic studies by Black at al., *Chem. Eng. Progr.*, 50, 403 (1980), *Ind. Eng. Chem.*, 50, 403 (1958)) show that n-pentane is a good entrainer for removal of water from ethanol. Like benzene or toluene, n-pentane forms a minimum boiling heterogeneous ternary azeotrope with ethanol and water. The ethanol product is withdrawn at the bottom of the azeotropic column. No phase splitting occurs in the columns, but two liquid phases of different compositions are formed in the decanter. The light phase contains 95% pentane, and the heavy phase contains 90% of water. The pentane in the light phase is returned to the column as reflux, and the heavy phase is concentrated using a two stage column.

Adsorption based separation processes for the removal of water from alcohols are described in, for example, U.S. Pat. No. 2,137,605; German Patent No. 1,272,293; and Canadian Patent No. 498,587, which collectively describe the use of either adsorbents or absorbents, including materials such as alumina and zeolites, for drying ethanol. The disclosures of these patents are incorporated herein by reference.

U.S. Pat. No. 4,277,635 describes the use of a crystalline silica polymorph (silicalite) for the adsorption of ethanol from an aqueous ethanol mixture, followed by recovery of the adsorbed, dehydrated ethanol by passing carbon dioxide gas through the silicalite bed. U.S. Pat. No. 4,273,621 describes a gas phase distillation dehydration process using crystalline zeolite molecular sieves, and a carbon dioxide gas stream as a drying aid. This reference teaches that zeolite sieves having a pore diameter of three Angstroms are useful; other adsorbents such as molecular sieves, carbon, alumina and silica would, in addition to adsorbing water; co-adsorb the ethanol and the carbon dioxide drying aid. The disclosures of these patents are incorporated herein by reference.

Also, materials such as fresh quicklime, anhydrous calcium chloride, anhydrous calcium sulfate, fused anhydrous potassium acetate, sodium acetate, barium oxide, silica gel, and various zeolites have been widely employed, silica gel and zeolites probably being the most commonly used. All of these reagents have disadvantages in that they must be extensively treated to remove the water before they can be reused.

Zeolite molecular sieves are adequate adsorbents for the removal of small amounts of water from organic solvents. By virtue of their small diameter (0.28 nm), the water molecules can easily penetrate the structural zeolite canals, while many organic molecules such as ethanol (0.44 nm), are excluded. The use of zeolites to remove water from ethanol is described in, for example, papers by Carton et al. (1987), Sowerby and Crittenden (1988), Ruthven (1984), Teo and Ruthven (*Ind. Eng. Chem. Process Des. Devel.*, 5, 17 (1986)), and Carmo and Gubulin (*Latin American Applied Research*, 31, 353 (2001)).

U.S. Pat. No. 4,345,973, the disclosure of which is incorporated herein by reference, proposes a method for dehydration and/or enrichment of aqueous alcohol mixtures wherein the mixtures in the vapor state are contacted with a dehydration agent composed of cellulose, caboxymethylcellulose, cornmeal, cracked corn, corn cobs, wheat straw, bagasse, starch, hemicellulose, wood chips, other grains, other agricultural residues or mixtures thereof.

Salt distillation processes are described in, for example, U.S. Pat. No. 1,474,216, which teaches the extractive distillation of ethanol from water using solutions of calcium chloride, zinc chloride, or potassium carbonate in glycerol. The vapor pressure of the dissolved salt is so low that it never enters the vapor phase. The disclosure of this patent is incorporated herein by reference.

Also, Johnson and Further (*Can. J. Chem. Eng.*, 43, 356 (1965)) reports that even a low concentration of potassium acetate eliminates the azeotropic behavior of the mixture. Rather then using a solvent that contains the dissolved salt, the salt can be added as a solid or melt directly into the column by dissolving it in the liquid reflux before it enters the column. At salt concentrations below the saturation point, almost pure ethanol can reportedly be achieved.

Salt distillation is accompanied by several problems, the most important of which is corrosion. Salt distillation columns require stainless steel or alloyed corrosion-resistant materials. Feeding and dissolving the salt also represents a potential problem; the solubility of salt is low in the reflux because it contains the more volatile component (ethanol), while the salt will be most soluble in the less volatile component accumulated at bottom. The presence of salts may increase the potential for foaming and possibility of salt crystallization in the column.

Detailed discussion of anhydrous ethanol production from a diluted aqueous solution of ethanol via extractive distillation with potassium acetate is discussed in Ligero et al., *Chemical Engineering and Processing*, 42(7), 543-552 (2003). In the first of two process flow sheets, diluted ethanol is directly fed to a salt extractive distillation column, and the salt is recovered in a multiple effect evaporator followed by a spray dryer. In the second flow-sheet, the concentrated ethanol from conventional distillation is fed to a salt extractive distillation column. In this case, salt is recovered in a single spray dryer. In both processes the recovered salt is recycled, the second process requiring less energy than the first.

U.S. Pat. No. 4,492,808, the disclosure of which is incorporated herein by reference, describes an extraction-based process for separating ethanol from an aqueous solution, wherein an ethanol-containing solution is extracted with $CO_2$, $C_2H_4$ or $C_2H_6$ in the form of liquids or supercritical gases. If $CO_2$ is used as the extracting agent, the extraction can take place at 30-150 atmospheres and at 0-150° C. In this process, the pressure of the ethanol-containing extract phase is reduced, and the ethanol is separated from the extraction agent by distillation. The ethanol, after the yeast is removed, is heated to 75° C., compressed by a pump to a pressure of 80 bar, and conveyed into mass transfer column, where it is contacted in countercurrent flow with the ascending supercritical $CO_2$ phase, causing the ethanol to transfer from the aqueous phase to the supercritical $CO_2$. At the bottom of the mass transfer column, the solution, which has an ethanol concentration of 2.2 wt. %, is removed. The pressure is reduced to atmospheric pressure, and the solution is degassed and returned to the alcohol fermenter.

The ethanol-containing solvent phase is fed from the top of the mass transfer column into the adsorber vessel and, at 75° C. and 80 bars, is exposed to granulated activated carbon. The ethanol is adsorbed by the activated carbon while the $CO_2$ is returned, with the aid of a compressor, to the bottom of the mass transfer column. The regeneration of 1 kg activated carbon requires 7.1 kg $CO_2$. Energy consumption in this example is about 4500 kJ/kg of product.

A distillation with chemical reaction process is a unit operation in which a chemical reaction and distillation are carried out simultaneously. Reactive distillation combines a chemical reactor and a distillation column in a single unit. Faitakis and Chuang (*Chem. Eng. Commun.*, 192, 1541

(2005), and *Ind. Eng. Chem. Res.*, 43, 762 (2004)) discuss the application of catalytic distillation to the dewatering of ethanol.

Catalytic distillation is a specific modification of reactive distillation and can be defined as a process in which heterogeneously catalyzed chemical reaction and separation occurs simultaneously in a single distillation column. Water is removed from ethanol by reaction with olefins, isobutylene being suitable for this purpose. The product of the reaction, t-butyl alcohol, must be removed from the ethanol by distillation. Unfortunately, water can be completely removed only by using large excess of isobutylene, and some of the ethanol is converted to its t-butyl ether.

Membrane systems have been employed to separate mixtures of miscible liquids by reverse osmosis. In such a process, the charge liquid is brought into contact with a membrane film, and one component of the charge liquid preferentially permeates the membrane. The permeate is then recovered as a liquid from the downstream side of the film. U.S. Pat. No. 5,139,677, the disclosure of which is incorporated herein by reference, describes the use of membranes with solutions containing 95 wt. % ethyl alcohol to recover product containing decreased quantities of water.

U.S. Pat. No. 5,028,240, the disclosure of which is incorporated herein by reference, describes the use of a freezing technique to purify ethanol. Most of the water from a dilute aqueous solution is removed by chilling sufficient to enable water to be separated in the form of ice crystals. Simultaneously, the remaining liquid is extracted at the same low temperature with a liquid organic solvent that is substantially immiscible with water but has high affinity to ethanol, causing alcohol to transfer to the organic phase. Ethanol separated from water and concentrated in an organic solvent such as toluene is useful as an addition to gasoline.

Water gas-shift reactions are employed in many industrial processes, including ammonia synthesis and hydrogen production. A water-gas shift reaction is a reversible, exothermic chemical reaction, frequently assisted by a catalyst, whereby steam reacts with carbon monoxide to produce carbon dioxide and hydrogen gas as shown below.

$$H_2O(g) + CO(g) \leftrightarrows CO_2(g) + H_2(g) \quad \Delta H = -41.2 \text{ kJ/mol.}$$

The water-gas shift reaction may actually occur in two reversible steps involving initial formation of formic acid from carbon monoxide and water. In a second step, the formic acid formed decomposes to hydrogen and carbon dioxide.

$$CO + H_2O \leftrightarrows HCO_2H$$

$$HCO_2H \leftrightarrows H_2 + CO_2$$

Many materials are capable of catalyzing the water-gas shift reaction, but two classes of materials used almost exclusively in the industry as shift catalysts are iron based catalysts and copper-zinc based catalysts.

Iron based catalysts are high-temperature catalysts, operating at temperatures of about 320-450° C. Iron oxide catalysts can tolerate small quantities of sulfur and are fairly rugged. Copper-zinc based catalysts are low-temperature catalysts that operate at temperatures of about 200-300° C. These catalysts have good activity at low temperatures and are attractive because the reaction equilibrium is more favorable at low temperatures. In addition to exhibiting high activity, low-temperature shift catalysts are very selective, with minimal side reactions.

Copper-zinc shift catalysts are extremely sulfur intolerant, being irreversibly poisoned even with small quantities of sulfur compounds. Guard beds are often used to reduce the sulfur level in the feed stream. The low temperature catalysts can be also irreversibly damaged by temperatures above 360° C.

W. Ruettinger, O. Ilinich, R. J. Farrauto, *J. Power Sources*, 118, 61-65 (2003) describe Selectra Shift™, developed by Engelhard Corporation, as an alternative to commercial CuZn catalyst for carrying out the water-gas shift reaction.

Another material that has received attention as an industrial water-gas shift catalyst is sulfided cobalt oxide-molybdenum oxide on alumina. This type of catalyst is completely insensitive to sulfur poisoning and possesses good activity even at low temperatures.

Water-gas shift catalysts are discussed in, for example, Cai et al., U.S. Pat. No. 6,627,572, the disclosure of which is incorporated herein by reference. Preferred water-gas shift catalysts include catalysts containing copper oxide, zinc oxide, aluminum oxide, and combinations thereof. A typical low temperature shift catalyst is reported to contain from about 30% to about 70% CuO, from about 20% to about 50% ZnO and from about 5% to about 40% $Al_2O_3$.

Industrial shift reactors are typically multistage adiabatic reactors with cooling between stages. The cooling assists the reaction to be closer to an optimum reaction path; heat exchangers or injection of condensate can be used for heat removal between individual stages. In the industry, configurations with three beds are commonly used, with the two top layers containing a high-temperature catalyst and a lower third bed containing a low temperature catalyst to complete the reaction.

U.S. Pat. No. 6,387,554, the disclosure of which is incorporated herein by reference, describes a process for the production of hydrogen and electrical energy from ethanol. The process is characterized by the partial oxidation/reforming of ethanol with water for hydrogen production which is subsequently fed to a fuel cell for production of electrical energy. The use of the water-gas shift reaction is reported as a means of removing carbon monoxide from the hydrogen formed, since excess carbon monoxide can interfere with the functioning of fuel cells. However, the process described in U.S. Pat. No. 6,387,554 does not produce dry ethanol.

Despite the technology described above, there remains a need to develop new methods to be able to economically separate water from alcohol on a large-scale. In particular, there is a need to separate water from ethanol on a large-scale and to produce ethanol that is nearly free of water.

SUMMARY OF THE INVENTION

The present invention is directed to a process and a suitable apparatus for producing dry alcohol wherein dry alcohol contains 0.5 wt. % or less of water and 99.5 wt. % or more of alcohol. A preferred alcohol includes ethanol.

The process includes at least one stage that includes contacting a gaseous feedstock, containing alcohol and water, with carbon monoxide in the presence of a water-gas shift catalyst, at a temperature sufficiently high so that carbon monoxide and water are at least partially consumed and carbon dioxide and hydrogen are formed, and thereby producing a mixture of alcohol and residual water.

The water-gas shift reaction used to dry the alcohol also liberates heat. Preferably the heat generated is used to increase the energy efficiency of the process. In one embodiment, the heat is used to generate high-pressure steam. The high-pressure steam may be used, for example, to convert feedstock to gaseous feedstock or in other stages of a production plant.

Depending on the amount of residual water present after the first stage, it may be necessary to dry the alcohol further. In one embodiment, the process includes a second stage and it may have additional stages. Each stage in the process may be adiabatic or non-adiabatic. The second stage includes the step of contacting the mixture of alcohol and residual water formed in the first stage with carbon monoxide in the presence of a water-gas shift catalyst, thereby removing a portion of the residual water. In the final stage of the process dry alcohol is produced.

A desirable apparatus for forming dry alcohol includes a reaction space including a first inlet for receiving a gaseous feedstock including alcohol and water, a gas inlet for receiving carbon monoxide, an effective amount of gas-shift catalyst, and an outlet for removing a product mixture. In a preferred embodiment, the apparatus also includes a means of removing heat and generating high-pressure steam.

A low-pressure process for producing methanol includes the step of contacting a gaseous feedstock, which includes water, with carbon monoxide in the presence of a water-gas shift catalyst at a temperature sufficiently high so that carbon monoxide and water are at least partially consumed and carbon dioxide and hydrogen are formed, and at a pressure below about 40 atmospheres, and thereby forming methanol.

DETAILED DESCRIPTION OF THE INVENTION

Figure 1:
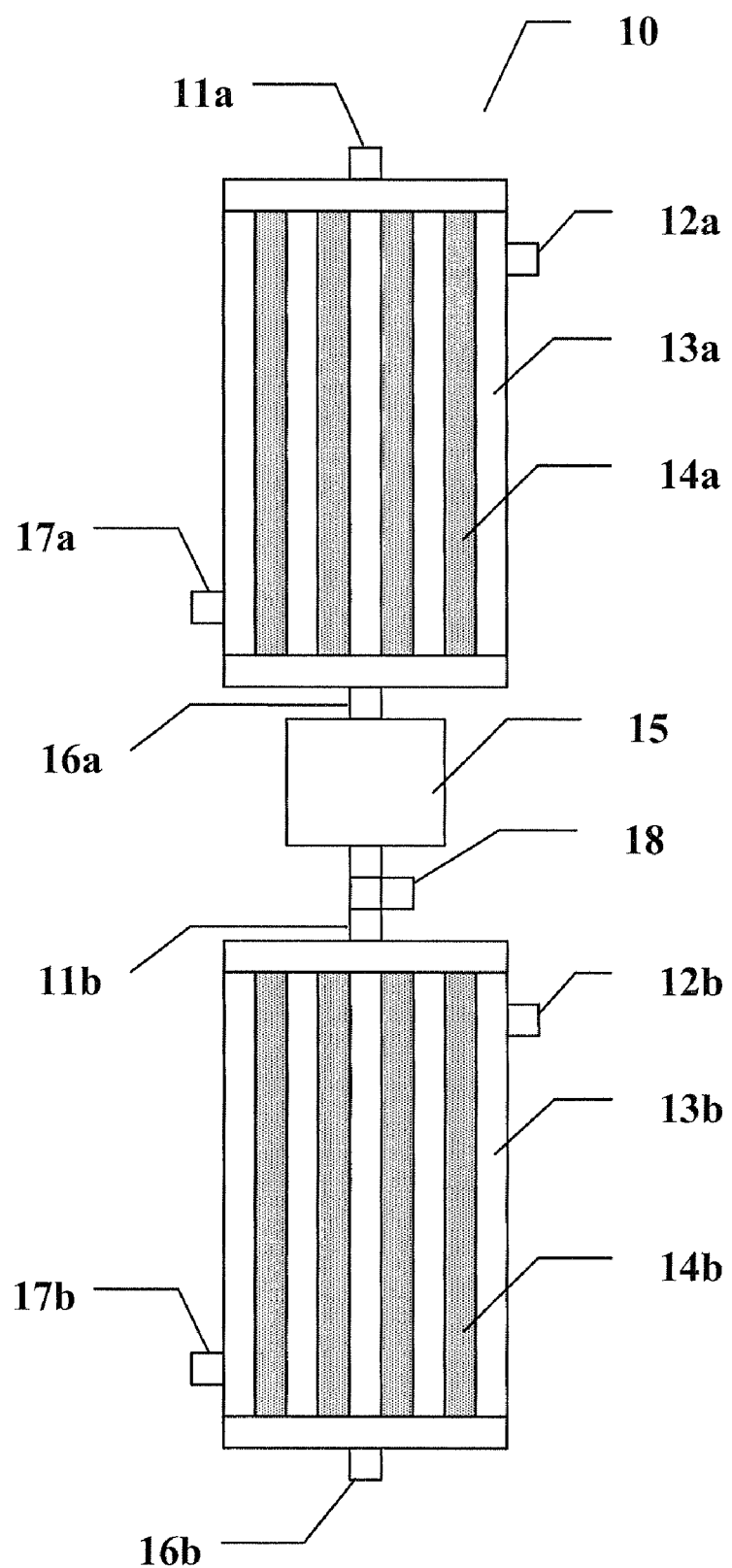
FIG. 1 is a schematic representation of a two-stage reactor.

The present invention provides an economical process for the production of dry alcohol from a feedstock of alcohol-water mixture by a catalytic reaction of the water with carbon monoxide in the presence of a water-gas shift catalyst. Dry alcohol contains 0.5% or less of water and 99.5% or greater of alcohol, desirably 0.3% or less of water and 99.7% or greater of alcohol, and preferably 0.1% or less of water and 99.9% or greater of alcohol by weight.

The alcohol may be any aromatic or aliphatic alcohol but is preferably an aliphatic alcohol. The alcohol may be a mixture of alcohols. In one embodiment, the alcohol includes a mixture of aliphatic alcohols, such as a mixture of ethanol and butanol. Desirably, the alcohol is ethanol or 1-butanol and in a preferred embodiment the alcohol is ethanol. In one desirable embodiment, the process produces absolute ethanol.

The feedstock for the process can be obtained from various sources. In one embodiment, the alcohol used in the process is ethanol and the feedstock is obtained by the hydration of ethylene.

In another aspect of the invention, the alcohol used in the process is ethanol obtained from a fermentation process, for example, by the fermentation of corn. For example, a mixture including ethanol can be formed in a fermentation apparatus and the liquid can then be separated from any solids present using a centrifuge. The liquid stream from the centrifuge, which typically contains 5-7 wt. % ethanol, can be fed to a first distillation apparatus, such as a beer column, where the concentration of alcohol is increased to at least about 30 wt. % and this material can be used as feedstock for the drying process. In one suitable embodiment of the invention, the feedstock is gaseous ethanol obtained from a distillation column, such as a beer column.

Suitably the feedstock contains at least 5% alcohol, more suitably at least 30% alcohol, desirably at least 50% alcohol, and preferably at least 80% alcohol. Desirably, the feedstock, which includes alcohol and water, is preheated in a heat exchanger. In one embodiment, the feedstock is in a gaseous phase and is heated to a temperature of about 180-350° C. and desirably to about 200-275° C.

The process includes at least one stage, wherein a stage includes a reactor including at least one reaction space. After heating, the gaseous feedstock is introduced into the reaction space. In one desirable embodiment, the process includes more than one stage, wherein each stage includes a reactor that has one or more reaction spaces.

The reaction space contains a water-gas shift catalyst and includes an inlet for feedstock and carbon monoxide and an outlet for removing product. In one embodiment, the reaction space operates as a non-isothermal, non-adiabatic reaction bed that can be cooled. A non-isothermal, non-adiabatic bed is one in which the temperature is not constant and heat can be transferred to or from the bed. The temperature in the reaction space is sufficiently high so that, in the presence of the catalyst, carbon monoxide and water are consumed and carbon dioxide and hydrogen are produced. The temperature should be below the temperature at which a significant amount of degradation of the alcohol occurs. For example, in the case of ethanol, under certain high temperature conditions, ethanol can dehydrate to ethylene and water. Preferably the temperature is below 500° C. The temperature is desirably about 180-350° C. and preferably about 200-250° C.

Desirably, carbon dioxide and feedstock, containing alcohol and water, are introduced into the reaction space in the presence of the catalyst. Suitably, carbon monoxide is present in a larger amount than the water, for example a 25%, 50% or even 100% or more excess of carbon monoxide relative to water is desirable (on molar basis). In the reaction space, carbon monoxide and water react in the presence of the catalyst, forming carbon dioxide and hydrogen. Thus, some or all the water is removed from the feedstock. After reaction, the product gas stream is allowed to exit the reaction space. In one embodiment, if sufficient water is removed, the dry ethanol is condensed. In another embodiment, the exiting product stream is used as feedstock for another stage of the process.

In one embodiment, a portion of the hydrogen gas that is formed by the water-gas shift reaction undergoes a further reaction with carbon monoxide in the presence of the catalyst to form methanol according to the following equation:

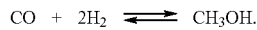

$$CO + 2H_2 \rightleftharpoons CH_3OH.$$

Methanol is a valuable chemical and has many industrial applications, for example, methanol is a raw material for the production of basic chemicals like formaldehyde and acetic acid. If desired, the methanol formed can be readily separated from the alcohol that is being dried by various well-known methods such as, for example, fractional distillation.

In one embodiment, the methanol formed is separated and used to produce biodiesel. The biodiesel process turns oils and fats into esters. Methanol can be used in the transesterification part of this process wherein glycerine is replaced with methanol and methyl esters are formed and biodiesel is produced.

Combustion of methanol also releases energy. In a further embodiment, methanol is used as fuel in a production plant.

Catalytic processes for the production of methanol were introduced by BASF in the 1920's. The BASF process used a mixture called synthesis gas, which includes carbon monoxide and hydrogen and frequently also includes carbon dioxide. The catalyst was based on $ZnO$—$Cr_2O_3$ compounds and operated at high temperatures (300° C.-400° C.) and at high pressures often between 250 and 350 atmospheres. Later, ICI developed a low pressure process using an improved catalyst of Cu/ZnO, however, this catalyst was often sensitive to process conditions. A more stable catalyst was developed in the 1960's using Cu/ZnO with support materials like $Al_2O_3$ and $Cr_2O_3$. The low pressure process typically takes place at pressure of 50-100 atmospheres and temperature of 220° C.-280° C. High pressure is required to drive the reaction, which involves a 3:1 volume reduction. Thus, the conversion of one mole of carbon monoxide and 2 moles of hydrogen to produce 1 mole of methanol is favored at high pressures.

In one embodiment, methanol is produced in the present process at very low pressures. Suitably, the pressure is below about 40 atmospheres, preferably at or below about 20 atmospheres, and desirably at or below about 10 atmospheres, or even at or below about 5 atmospheres. In one embodiment, the pressure is about 10 atmospheres to about 15 atmospheres. When the process includes the water-gas shift reaction, the methanol synthesis reaction can be carried out efficiently at low pressures.

The water-gas shift catalyst is any catalyst that catalyses the reaction of carbon monoxide and water to produce carbon dioxide and hydrogen. A catalyst is a substance that increases the rate of a reaction by decreasing the activation energy of a reaction but is not consumed in the overall reaction. Suitable water-gas shift catalysts include those containing iron oxide, copper-zinc, sulfided cobalt oxide-molybdenum oxide on alumina, and Selectra Shift™ catalyst as previously described. Desirably, the catalyst is a low-temperature catalyst, wherein a low-temperature catalyst is effective below a temperature of 350° C. and desirably below 275° C. In one embodiment, the catalyst includes copper-zinc (CuZn), for example, Cu/ZnO or Cu/ZnO/$Al_2O_3$. In another embodiment, the catalyst includes Selectra Shift™ available from Engelhard Corp. In a further embodiment, the catalyst includes sulfided cobalt oxide-molybdenum oxide on alumina. In a still further embodiment, the catalyst is a zinc-chromium-copper oxide catalyst.

Raney copper may also be useful as a catalyst. For example, N. J. Coville et al., *Applied Catalysis A: General*, 164, 185-195 (1997), describe the use of Raney copper in the water-gas shift reaction. Especially useful are Raney copper catalyst containing zinc oxide. Raney copper may also be prepared in situ by reduction of copper oxide.

In one desirable embodiment, the water-gas catalyst includes at least two active components. Without being bound by any particular theory, the water-gas shift catalyst can be thought of as providing at least two functions: carbon monoxide adsorption and dissociation of water, and a chemical reaction that produces carbon dioxide and hydrogen. Thus, it may be useful to have a catalyst that contains at least two components wherein each component facilitates a part of the overall reaction. Useful metals for one component of the catalyst include Pt, Ru, Pd, Cu, Co, Mo, Ag, Au, Rh, and Fe and their oxides as well as combination thereof. Useful materials for a second component include oxides of V, Sn, and Ce or combinations thereof. An example of a suitable two-component catalyst is one that contains vanadium oxide and also includes Fe, Co, Cu, Mo, W, Mn, Ni, Ag, Sn, Se, Pb, or Bi or an oxide thereof. Another example of a suitable catalyst is one that contains tin oxide and also includes Mo, Mn, Fe, Co, Ni, Cu, Bi, W, Cd, Ge, or Pb or an oxide thereof. A further example of a suitable catalyst is one that includes cerium oxide and also includes Mo, Mn, Fe, Co, Sn, W, Ru, or Ge or an oxide thereof.

In a further embodiment, especially if it is desirable to promote the formation of methanol as described previously, it may be useful to include a catalyst containing cesium. An example of useful catalyst includes Cs—Cu/ZnO/$Al_2O_3$ as described by M. Xu et al., *Journal of Catalysis*, 171, 130-147 (1997), the entire disclosure of which is incorporated herein by reference.

The first drying stage described above may be followed by one or more adiabatic or non-adiabatic additional drying stages to further remove water from the alcohol as needed. For example, the product from the first drying stage including carbon dioxide, hydrogen, water, and residual alcohol can be used as feedstock for the second drying stage. In one suitable embodiment, the process includes at least one adiabatic stage. In one embodiment, the process comprises a series of reactors.

During the operation of catalytic fixed bed reactors, there exists an optimum temperature profile that will afford the maximum yield of product using the minimum amount of catalyst. It is very difficult to achieve this optimum profile by using only one reactor. It is desirable to use a series of reactors, which allows more flexibility in operation and more control over the system parameters, such as temperature. This can allow the process to be operated in a safer and more economical manner. Some stages (reactors in series) can be adiabatic and some can be non-adiabatic.

In a preferred embodiment, the process comprises a first drying stage and at least one additional drying stage. Desirably, the subsequent drying stage(s) includes at least one reaction space that includes a water-gas shift catalyst and an inlet for injecting the product stream from the previous stage, an optional inlet for carbon monoxide, and an outlet for removing product. The type of water-gas shift catalyst in the second reaction space may be the same as that in the first or different. In the second reaction space, the temperature is sufficiently high that carbon monoxide and water can react in the presence of the catalyst, forming carbon dioxide and hydrogen, and consequently removing some or all the water from the alcohol. After reaction, the product gas stream is allowed to exit the reaction space. The temperature in the second and any subsequent stage reaction spaces is desirably about 180-250° C. and preferably about 200-230° C.

In one suitable embodiment, the process includes cooling the product stream between stages. Desirably, the stream of gases leaving the final reaction space is also cooled. Cooling can be achieved by use of a heat exchanger. Preferably the heat exchanger operates by transferring the heat to cooling water, wherein the cooling water is vaporized to form steam. Preferably high-pressure steam is formed, that is steam having a pressure greater than 1 atmosphere, desirably greater than 20 atmospheres, preferably greater than 50 atmospheres, or even greater than 100 atmospheres. The high-pressure steam formed can then be used to make the drying process energy efficient. For example, the high-pressure steam could be used to heat feedstock to aid in the formation of the gaseous feedstock used in the process. The high-pressure steam could be used to generate electricity by well-known methods. If the process is being used in a production plant, the high-pressure steam could be used in the operation of the plant. When multiple stages are present, cooling between the stages can keep the process under almost isothermal conditions.

Another useful means of removing heat is by direct injection of the liquid form of the alcohol that is being dried. Vaporization of the liquid alcohol removes heat. The injection can be directly into the product stream in the reaction space or directly into the product stream between stages. When multiple stages are present, cooling between stages can keep the process under almost isothermal conditions.

In certain embodiments, it is desirable to operate the process under a pressure of greater than 1 atmosphere to ensure good recovery of the dry alcohol that is formed and so that, when in the gaseous state, the alcohol is not lost to the environment. For example, it may be desirable to carry out the water-gas shift reaction under a pressure of about 1 atmosphere to about 25 atmospheres, and desirably, under a pressure of about 3 atmospheres to about 20 atmospheres, and preferably at about 10 atmospheres to about 15 atmospheres.

In one embodiment, when multiple stages are present, additional carbon monoxide is injected into the product stream between stages. For example, carbon monoxide may be added to the product stream exiting the reaction space(s) in a first stage, and before the product stream enters the reaction space(s) in a second stage. Carbon monoxide can be generated by various methods, for example, by the combustion of a carbon source. In another embodiment, individual reaction spaces may have an inlet for injecting carbon monoxide.

In another embodiment, the product gas exiting the reaction space(s) of one stage is cooled sufficiently to condense the alcohol and any water present to the liquid state. After cooling, the condensate is separated from the mixture of gases, such as carbon monoxide, carbon dioxide, and hydrogen, which may be present. Preferably, carbon dioxide is then removed from the mixture of gases, for example, by reaction with an amine, such as ethanolamine. Suitably, any unreacted carbon monoxide can be recycled.

If the condensed alcohol is not sufficiently dry, the alcohol can be evaporated and injected into a second or subsequent stage of the reactor. The dry alcohol product exiting the final stage of the reactor has a concentration of at least 99.5 wt. %, suitably at least 99.7% and preferably about 99.9 wt. % alcohol. The dry alcohol contains 0.5 wt. % or less of water, suitably 0.3 wt. % or less, and preferably 0.1 wt. % or less of water.

In one desirable embodiment, the process includes at least one tubular reactor, also referred to as a "shell and tube heat exchanger." The tubular reactor is a non-adiabatic reactor consisting of a plurality of tubes, wherein the tubes contain the water-gas shift catalyst. The catalyst may be on a suitable support that provides a high surface area and allows gas to pass through or around the support and to contact the catalyst. For example, the support may be formed of zeolite materials. The reactant gas, containing alcohol, water, and carbon monoxide, enters the tubes wherein a portion of the water is removed and carbon dioxide and hydrogen are formed. This process also generates heat. The tubular reactor is adapted so that a cooling liquid, such as water, flows outside the tube walls but within a shell.

In order to a achieve efficient heat transfer it is generally desirable to have a large heat transfer area. Thus, it is usually desirable to have many tubes of relative small diameter rather than a smaller series of large tubes. One skilled in the art can easily determine the optimum tube size and number for a given volume of alcohol to be dried without undue experimentation.

In a preferred embodiment, heat is removed from the tubular reactor by circulating cooling water through the shell; the heat converts the cooling water to high-pressure steam. As describe previously, the high-pressure steam can be used for various purposes to make the process more energy efficient. For example, to heat feedstock, to generate electricity, or to operate other stages of a production plant.

In another suitable embodiment, the reactor includes 100 or more, 500 or more, or even 1000 or more, tubular reactors. In a further embodiment, a desirable tubular reactor has cylindrical shape with a length dimension that is at least 5 times and desirably at least 10 times its internal diameter dimension. In a another embodiment, a tubular reactor has a length dimension in the range of 1 m to 25 m and desirably in the range of 1 m to 5 m. In a further embodiment, a tubular reactor has an internal diameter dimension in the range of 1 cm to 25 cm, and desirably in the range of 1 cm to 10 cm. In a still further embodiment, a tubular reactor has a length dimension of 1 m or greater and an internal diameter dimension of 10 cm or less.

In a further embodiment, the process includes a fixed-bed reactor. The reactor bed includes a support that provides a high surface area for the water-gas shift catalyst and allows reactant gases to pass through or around the support and to contact the catalyst. For example, the support may be formed of zeolite materials. The reactor is adiabatic; heat is not removed from the reactor during the reaction process. However, heat may be removed from the product steam after leaving the reaction bed by use of a heat exchanger. Reactant gases may also be heated or cooled by means of a heat exchanger before entering the reactor.

In a further embodiment of the invention, the process includes at least one stage that includes a gas-water shift catalyst as described above and at least one further stage that includes an alternative means of removing water from alcohol. For example, the alternative means of removing water from alcohol may include removing water from alcohol by azeotropic or extractive distillation based processes, the use of a sorbent such as molecular sieves, or by salt distillation processes, or by other techniques known in the art some of which have been described previously. It may be useful to employ some of these techniques in a stage of the current process if ultra-dry alcohol is desired.

FIG. 1 shows a schematic representation of a two stage reactor (10). Gaseous aqueous ethanol and carbon monoxide enter the first stage through inlet port 11a. The first stage includes tubular reactors (14a) containing catalyst material. The reactors are surrounded by cooling spaces (13a) which are useful for controlling the temperature of the reactors. Cooling agents, such as vaporizing pressurized water to produce high-pressure steam, can enter the cooling spaces by means of inlet port 17a and exit via outlet port 12a.

A gaseous mixture of ethanol, water, and carbon monoxide enter the tubular reactors and water is removed by means of the water-gas shift reaction. Ethanol and any remaining water exits the first stage of the reactor by means of exit port 16a and enters a heat exchanger, 15. The temperature of the aqueous ethanol is adjusted by means of the heat exchanger and additional carbon monoxide is added, as needed, by means of inlet port 18. In one embodiment, the heat exchanger produces high-pressure steam. The gaseous mixture then enters the second stage of the reactor via inlet port 11b. The second stage includes tubular reactors (14b) as well as cooling spaces (13b) having inlet and exit ports 17b and 12b. After passing through the tubular reactors, the dry ethanol exits via exit port 16b.

The process of the present invention is illustrated by the examples presented below. The experiments are simulated using computer modeling. The catalyst is a zinc-chromium-copper oxide low temperature catalyst and the chemical kinetics used for the reaction are those reported by Temkin et al., Kinetics And The Mechanism Of The Catalytic Reaction Of Carbon Monoxide With Water Vapor I. Reaction Over An Iron-Chromium Oxide Catalyst., *Kinetika i Kataliz*, 6(6), 1057-68 (1965) and Kinetics And The Mechanism Of A Catalytic Reaction Of Carbon Monoxide With Water Vapor. II. Reaction Over A Zinc-Chromium-Copper Oxide Catalyst, *Kinetika i Kataliz*, 6(6), 1115-7, (1965). The reactor was mathematically described by the following equations and by using the material and enthalpy balance for tubular PFR as reported by Froment, F. and K. B. Bischoff, *Chemical Reactor Analysis and Design*, 2nd Ed., 664 (1990). Equations were integrated using Maple 9.5 software available from Maplesoft™ Corporation.

$$w \frac{dX_A}{dx} = r_A$$

$$w \sum_{i=1}^{n} \Theta_i Cp_i \frac{dT}{dx} = (-\Delta_r H) r_A$$

$$r_A = k \frac{P_{H_2O} P_{CO}}{A P_{H_2O}} \left[ 1 - \frac{P_{H_2} P_{CO_2}}{K_P P_{H_2O} P_{CO}} \right]$$

In the equations, $r_A$ is the reaction rate, k and A are constants, K is the equilibrium constant, $P_{H2O}$, $P_{CO}$, $P_{CO2}$, and $P_{H2}$ are the partial pressures of the corresponding gas.

Inlet temperature of reactants is 523 K (250° C.). Pressure through the bed is constant and equal to 3.4 atm (50 Psia). Flow of feed stream is 45000 lbs/hour (ethanol and water). After each stage, the gaseous mixture is cooled down to 250° C., which corresponds to the inlet temperature of the next stage.

The composition of the gas streams is given in molar fractions. The conversion of $H_2O$ is given as:

$$X_{H2O} = \frac{N^0_{H2O} - N_{H2O}}{N^0_{H2O}} = \frac{x^0_{H2O} - x_{H2O}}{x^0_{H2O}}$$

where $N_{H2O}^0$ and $x_{H2O}^0$ represent the moles and molar fraction respectively of water present initially in the mixture and $N_{H2O}$ and $x_{H2O}$ represent moles and molar fraction of water in the exit stream. If all the water was consumed by the reaction, then $N_{H2O}$ and $x_{H2O}$ would equal to zero and the conversion, $X_{H2O}$, would equal to 1, and the percent conversion would be 100.

EXAMPLE 1

Inventive-Simulation

Water-gas shift in the adiabatic multistage reactor with cooling between stages—10 wt % of water in the feed.

The reactor is 2 meters long and consists of 4000 tubes, each 1" in diameter. The reactor operates at 3.4 atm of pressure. The reactor has three quenching points at 10, 25 and 50% of reactor length, and thus, the reactor is divided into four stages. The first stage is 0.2 meters long, the second stage is 0.3 meters long, the third stage is 0.5 meters long, and the final stage is 1 meter long.

Figure 2A:
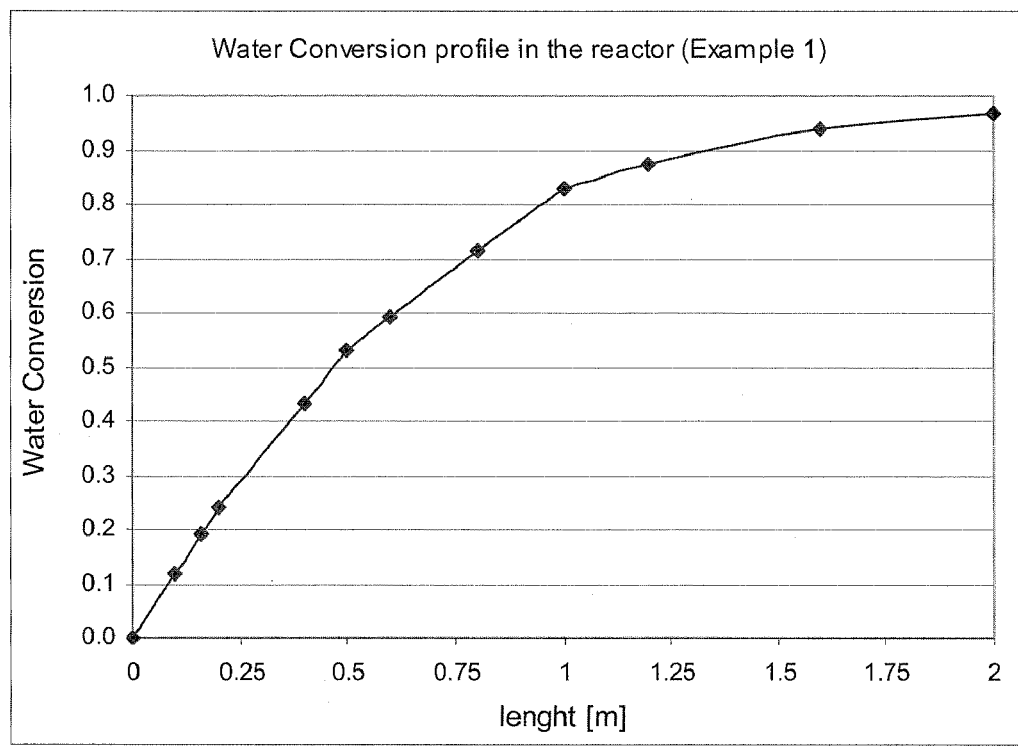
FIG. 2a shows the water conversion profile for the reactor in Example 1.
Figure 2B:
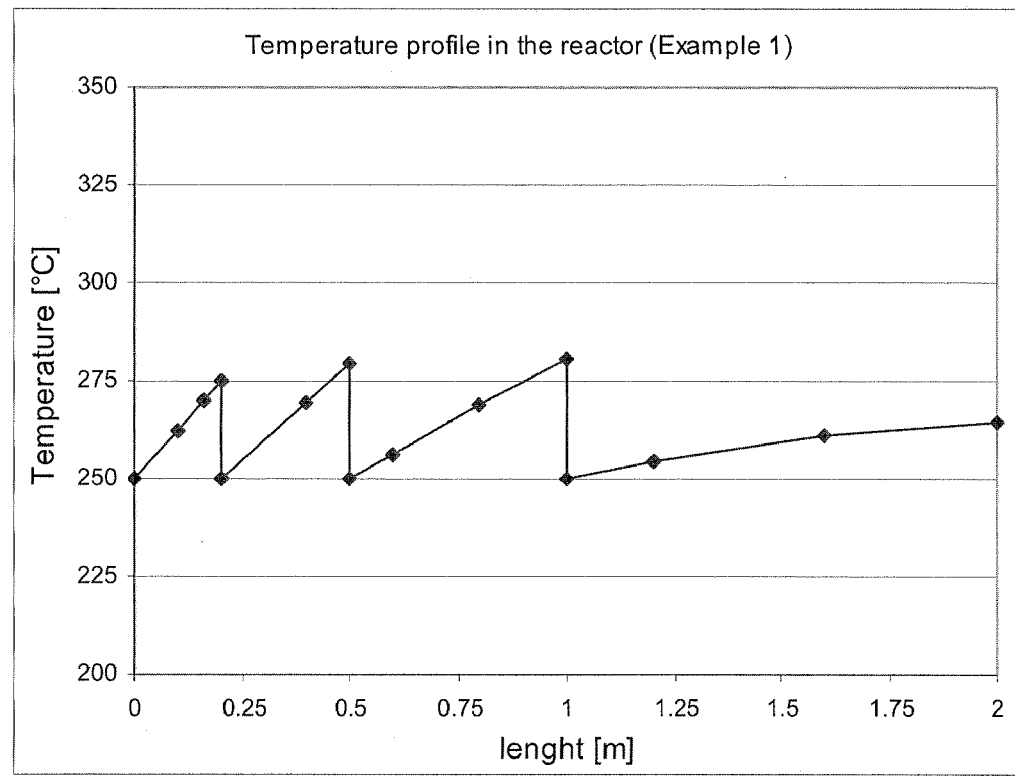
FIG. 2b shows the temperature profile for the reactor in Example 1.

A feed of 20,510 kg/hr (45,000 lb/hr) of a mixture of ethanol and water containing 10 wt % of water is injected at a temperature of 250° C. into the four-stage adiabatic reactor with cooling between stages. The amounts of catalyst at the four stages are, in order, 405, 608, 1013 and 2026 liters. The molar excess of CO relative to $H_2O$ is 2 and the velocity in the bed is 1.3 m/sec. The exit temperature after each stage is lowered to 250° C. by use of a heat exchanger. The conversion ratio at the four stages is 0.242, 0.530, 0.828 and 0.969, and the exit temperatures are 275, 278.9, 280.5 and 264.4° C., respectively. FIG. 2b shows the temperature profile for the reactor in this example; each stage operates as adiabatic (linear increase in the temperature). At the end of the stage, reacting mixture is cooled down. FIG. 2a shows the water conversion profile, which is the water removed by the water-gas shift reaction relative to water initially present.

The composition of the final exit gas in molar fractions is 0.47% water, 15.81% CO, 14.87% $CO_2$, 14.87% $H_2$ and 53.97% ethanol. After condensation of ethanol and water and absorption of the $CO_2$ in ethanolamine, the gas contains 51.53% CO and 48.47% $H_2$. In the process, 96.9% of the water is removed, and the purity of the ethanol after condensation is 99.7 wt %.

The above example would apply to fixed packed beds, not in tubes, but rather in cylindrical vessels, with interstage cooling using heat exchangers.

EXAMPLE 2

Inventive-Simulation

Water-gas shift in the adiabatic multistage reactor with cooling between stages—20 wt % of water in the feed.

Figure 3A:
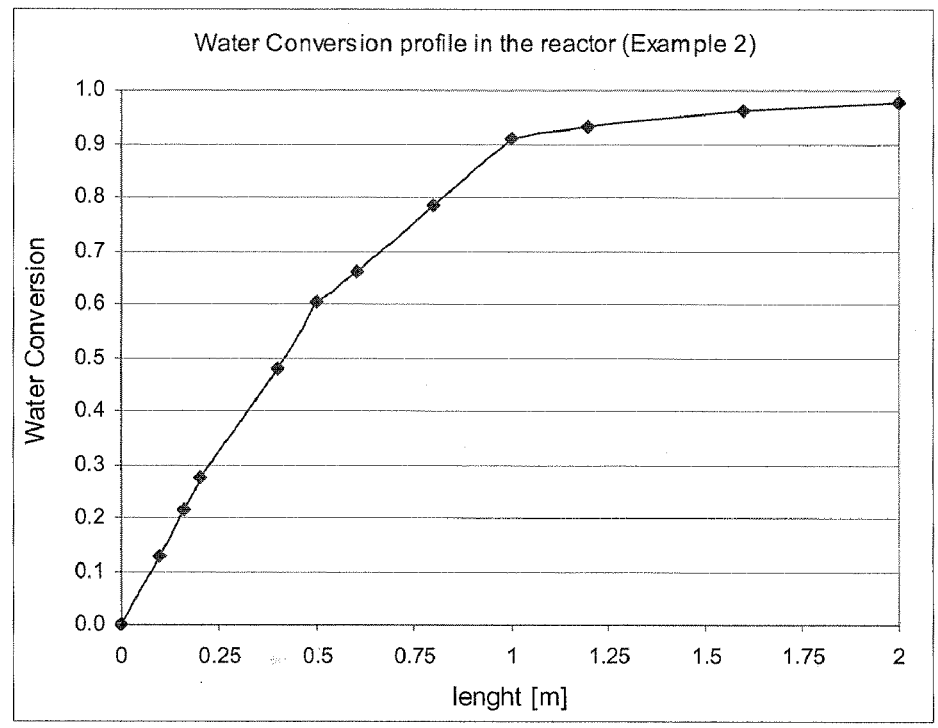
FIG. 3a shows the water conversion profile for the reactor in Example 2.
Figure 3B:
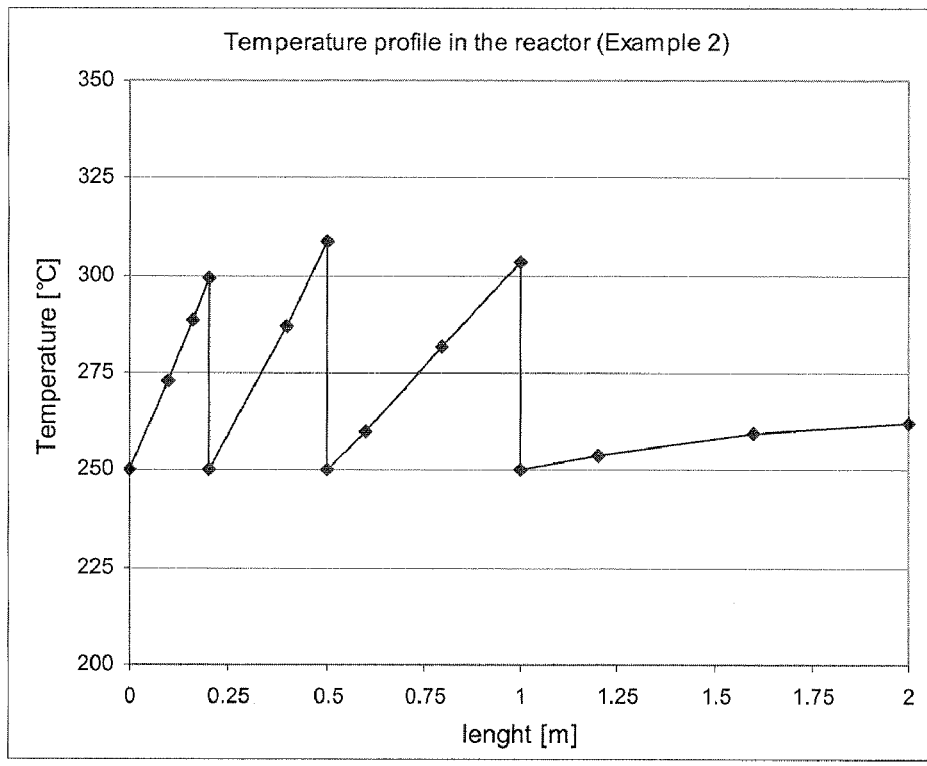
FIG. 3b shows the temperature profile for the reactor in Example 2.

The conditions are the same as in Example 1, except that the inlet gas contains 20 wt % of water. The velocity in the bed is 1.8 m/sec. The conversions at the four stages are 0.275, 0.604, 0.909 and 0.978, and the exit temperatures are 299.2, 308.5, 303.8 and 262.3° C., respectively. Water conversion and Temperature profiles are shown on FIG. 3a and FIG. 3b, respectively.

The composition of the final exit gas is 0.48% water, 22.39% CO, 21.43% $CO_2$, 21.43% $H_2$ and 34.27% ethanol (molar fractions). After condensation of ethanol and water and absorption of $CO_2$ in ethanolamine, the gas contains 51.09% CO and 48.91% $H_2$. In the process, 97.8% of the water is removed, and the purity of the ethanol after condensation is 99.5 wt %.

EXAMPLE 3

Inventive-Simulation

Water-gas shift reaction in a cooled first stage tubular reactor (thus non-adiabatic) is followed by an adiabatic 2 stage reactor with cooling between stages.

A reactor inlet stream is produced by mixing pure CO from a carbon combustor with overhead vapor from a beer column containing 66 wt % water and 20% of recycle stream. Recycle stream refers to a gas stream that was used in a previous process cycle and in which any ethanol and water were removed by condensation, and $CO_2$ was removed by an absorptive means. The recycle stream includes CO as well as $H_2$ that was produced in a previous cycle.

The mixture, which contains 33.33% water, 16.66% ethanol, 33.33% CO, 8.33% $CO_2$ and 8.33% $H_2$ is injected at a rate of 4,574 kmol/hr into a first stage tubular non-isothermal non-adiabatic reactor with 6,000 tubular reaction spaces (tubes), 2.54 cm (1 inch) internal diameter, each 6 m long, operating at 227° C. (inlet) and 5 atmospheres pressure. The stream enters each of the tubular reaction spaces, which contain water-gas shift catalysis (see the Table for the amount of total catalyst) and wherein water is removed from the stream. The reactor is cooled by boiling pressurized water at 26 atmospheres (boiling point 226.85° C.), resulting in the generation of steam.

Figure 4A:
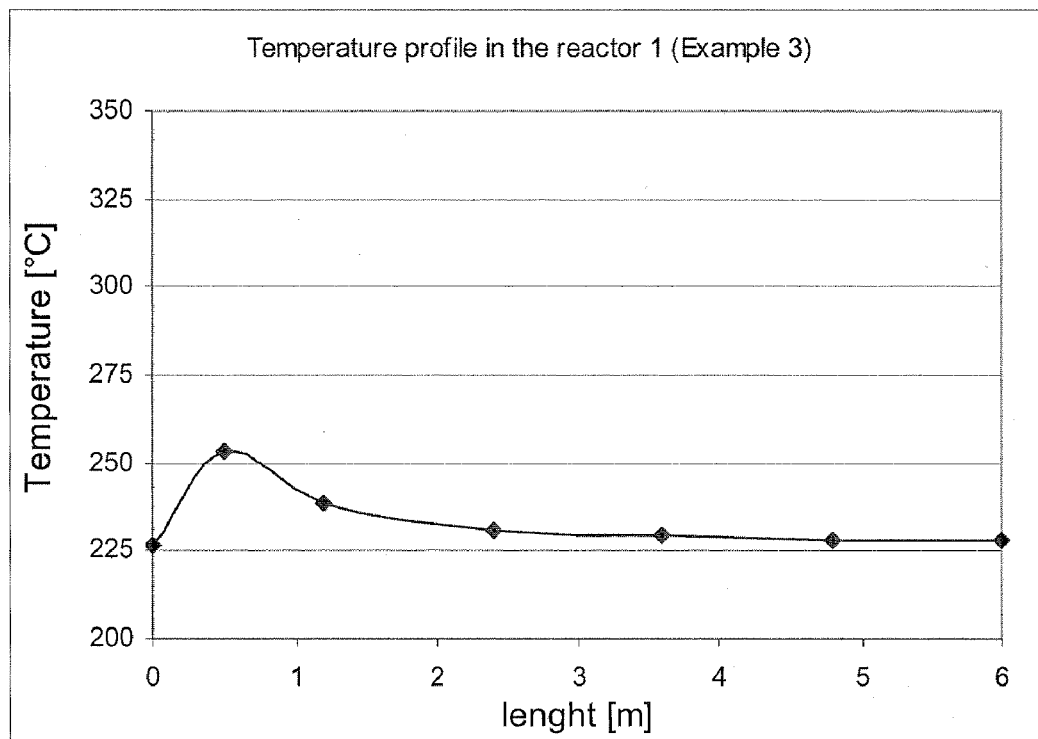
FIG. 4a shows the temperature profile for the reactor 1 in Example 3.
Figure 4B:
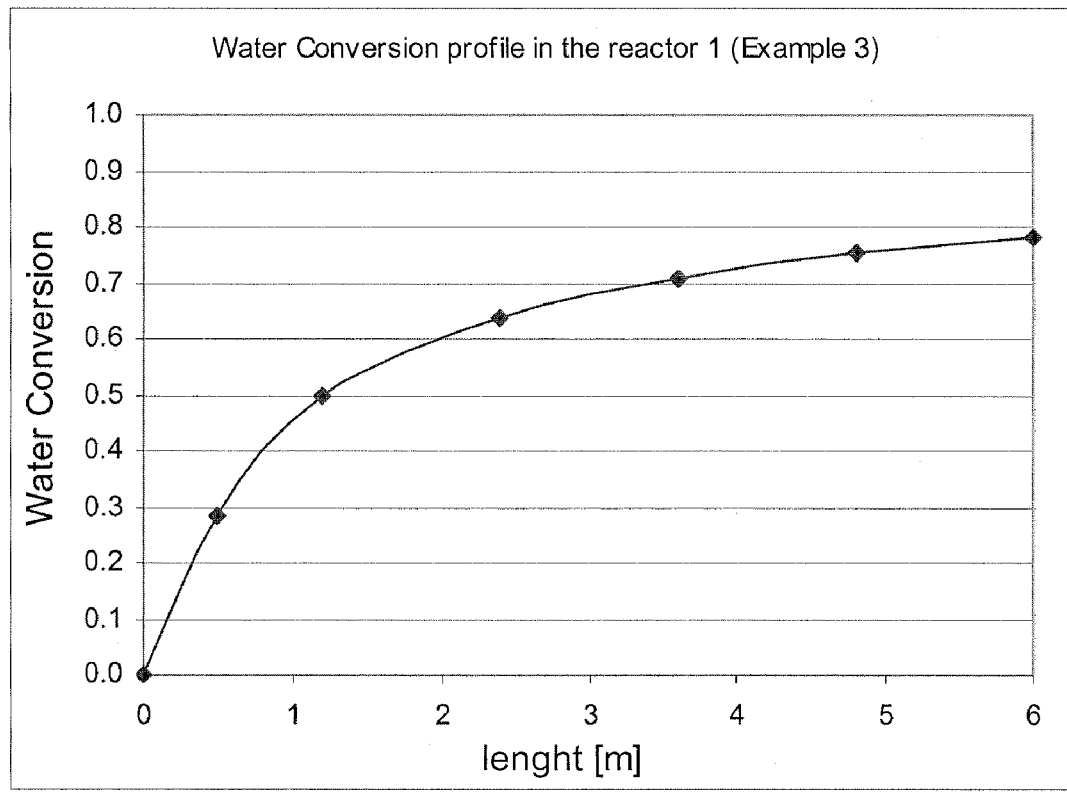
FIG. 4b shows the water conversion profile for the reactor 1 in Example 3.

FIG. 4a shows the temperature profile for the first tubular reactor in this example; the reactor has a hot spot of 253° C. FIG. 4b shows the water conversion profile, which is the water removed by the water-gas shift reaction relative to water initially present, for the first tubular reactor. The final conversion ratio of this reactor is 0.784.

The exit gas, which has a composition of 16.66% ethanol, 8.29% water, 8.2% CO, 33.5% $CO_2$ and 33.5% $H_2$, (molar fractions) is condensed to remove the water and alcohol as a liquid. The liquid is then evaporated and mixed with 834 kmol/hr of pure CO coming from the combustor, and the stream is introduced into an adiabatic reactor including a first and second stage and containing 12.7 $m^3$ of catalyst at 217° C. and 4 atmospheres pressure. The cooling between the first and second stages lowers the temperature from 331° C. to 237° C. The exit conversion is 0.744 from the first stage and 0.9837 from the second stage. The exit temperature from the second stage is 273° C., and the exit composition of the gas is 39.3% ethanol, 0.28% water, 22.33% CO, 19.1% $CO_2$, and 19.1 mol % $H_2$ (molar fractions). The purity of the ethanol after condensation is 99.72 wt %.

Figure 5A:
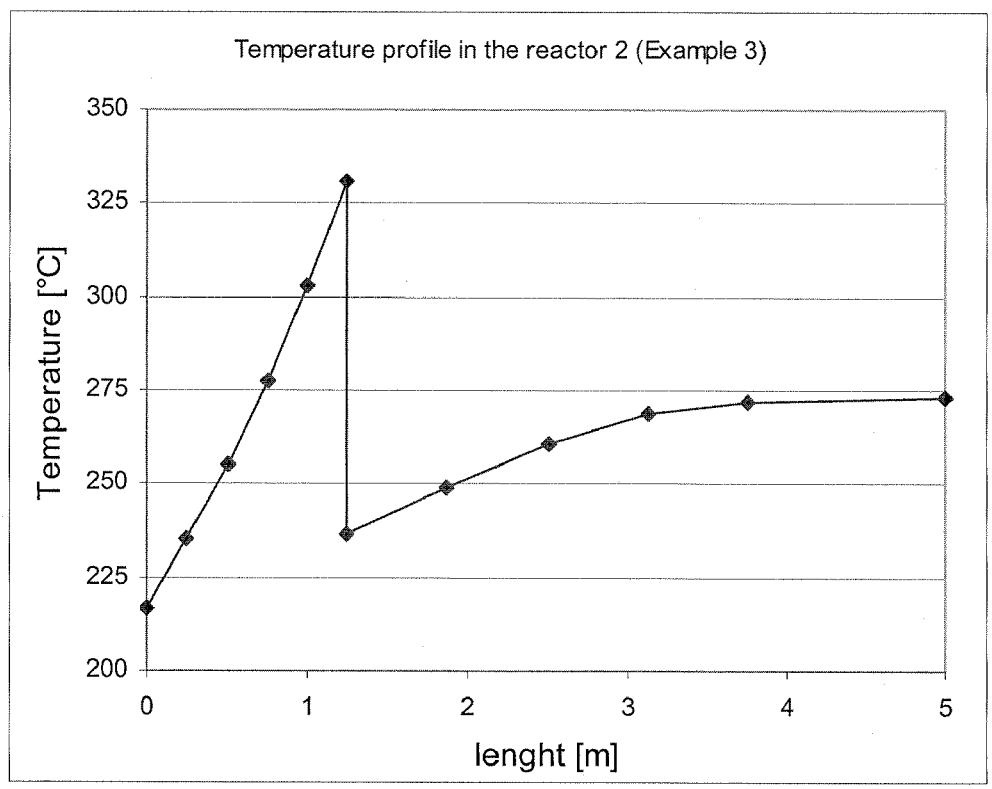
FIG. 5a shows the temperature profile for the reactor 2 in Example 3.
Figure 5B:
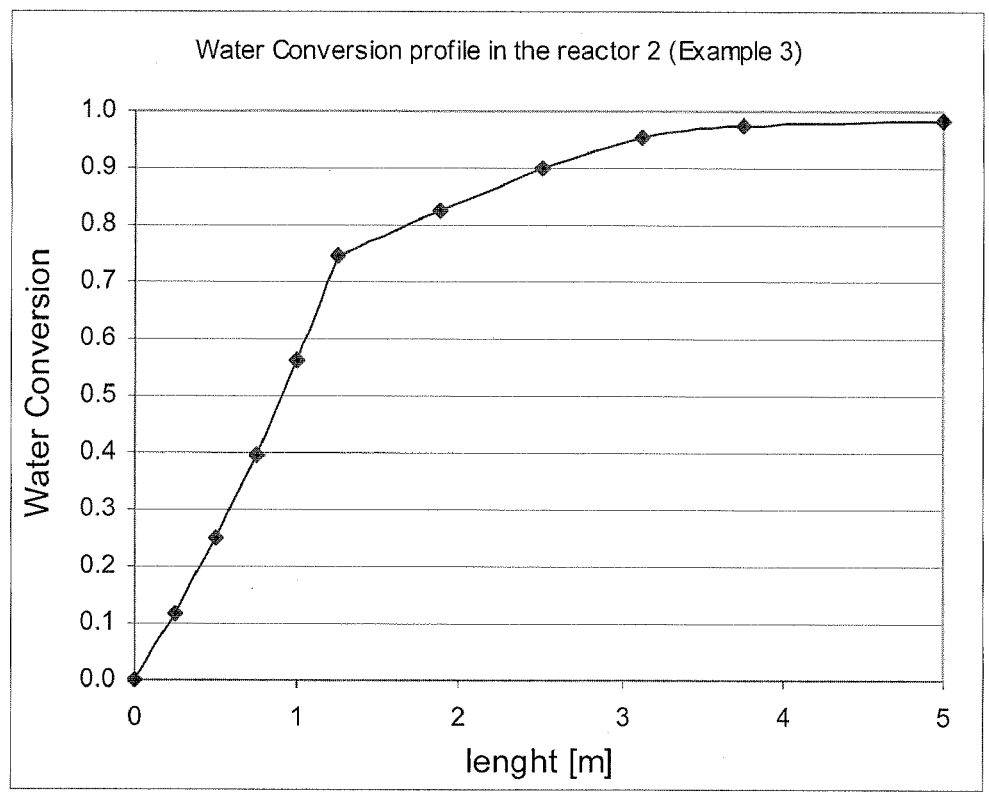
FIG. 5b shows the water conversion profile for the reactor 2 in Example 3.

FIG. 5a shows the temperature profile and FIG. 5b shows the water conversion profile for the second reactor. Nearly all the water is removed after the final stage.

EXAMPLE 4

Inventive-Simulation

Water-gas shift reaction in cooled first tubular reactor followed by an adiabatic 2 stage reactor with cooling between stages.

A feed of 2265 kmol/hr of a mixture containing 29.85% water, 33.66% ethanol, 29.85% CO, 3.32% $H_2$ and 3.32% $CO_2$ is injected in a tubular non-isothermal non-adiabatic reactor with 6,000 tubular reaction spaces (tubes), 2.54 cm (1 inch) internal diameter, each 6 m long and operating at 227° C. (inlet) and 5 atmospheres pressure. See the Table for the amount of total catalyst. This mixture is produced by mixing the gas produced by the combustion in a furnace of carbon in a stream of oxygen and $CO_2$ with the stream of water and alcohol containing 47 wt %, water from the beer column and 10% of a recycle stream containing only CO, $CO_2$ and $H_2$ from a downstream part of the process. The reactor is cooled by boiling pressurized water at 26 atmospheres (boiling point 226.85° C.), resulting in the generation of steam.

Figure 6A:
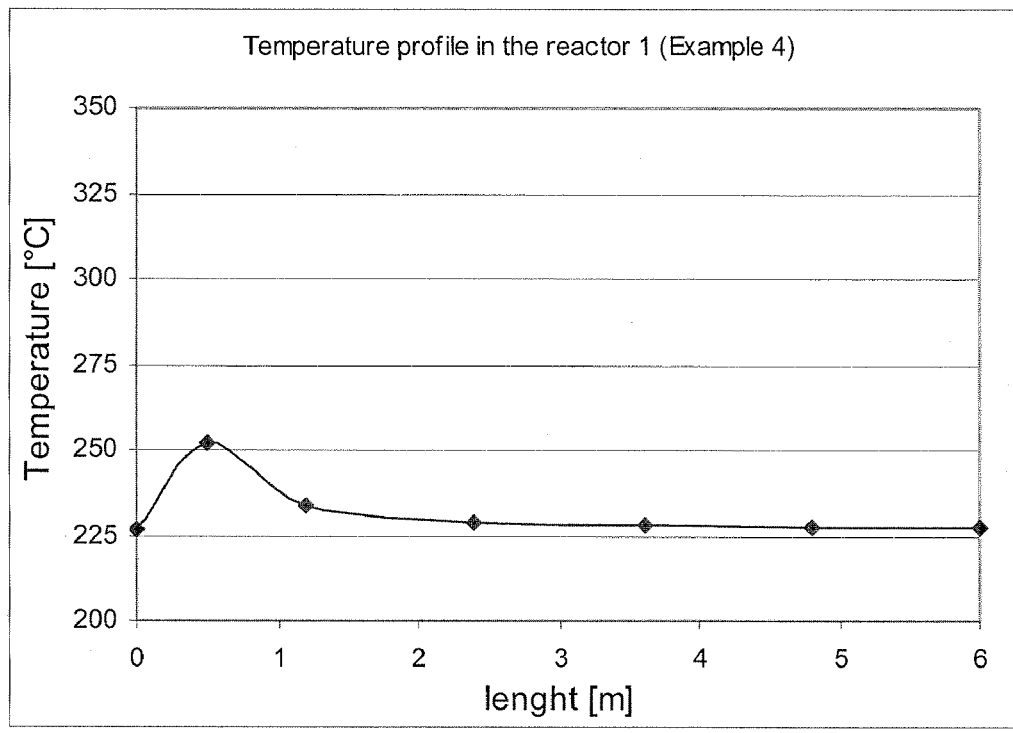
FIG. 6a shows the temperature profile for the reactor 1 in Example 4.
Figure 6B:
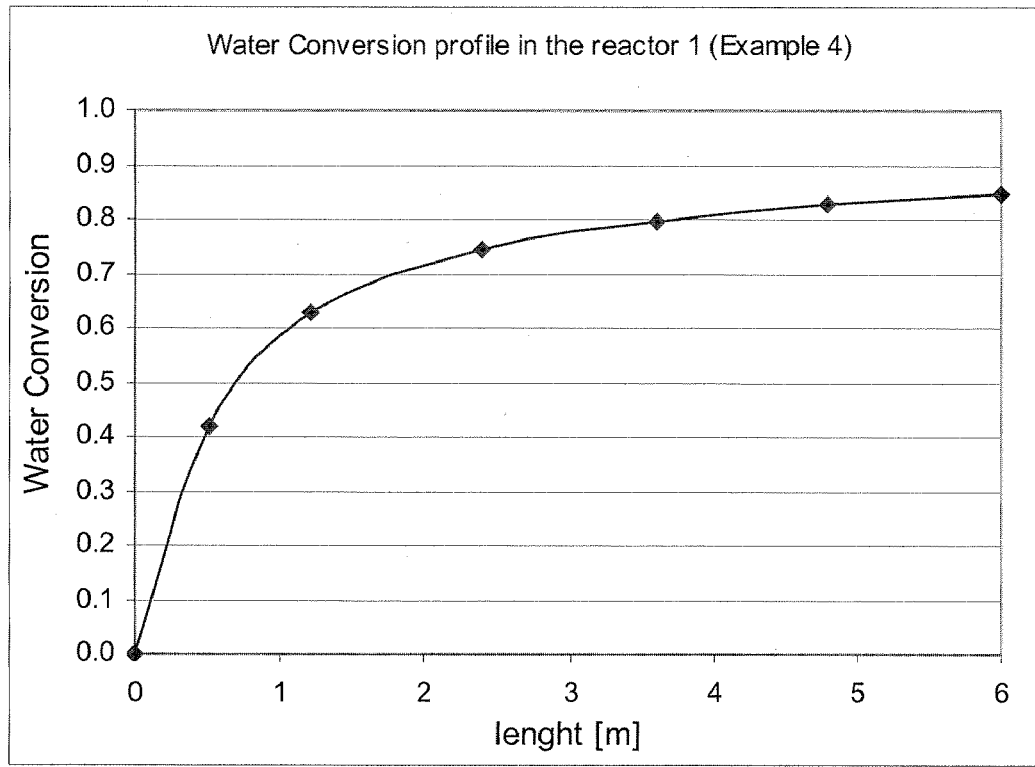
FIG. 6b shows the water conversion profile for the reactor 1 in Example 4.

The reactor has a hot spot of 252° C., and the exit conversion ratio is 0.84. FIG. 6a shows the temperature profile for the first non-adiabatic tubular reactor in this example. FIG. 6b shows the water conversion profile for first reactor. The composition of the exit gas is 33.66% ethanol, 4.53% water, 4.53% CO, 28.64% $CO_2$ and 28.64% $H_2$ (molar fractions). The exit temperature is 227° C.

Figure 7A:
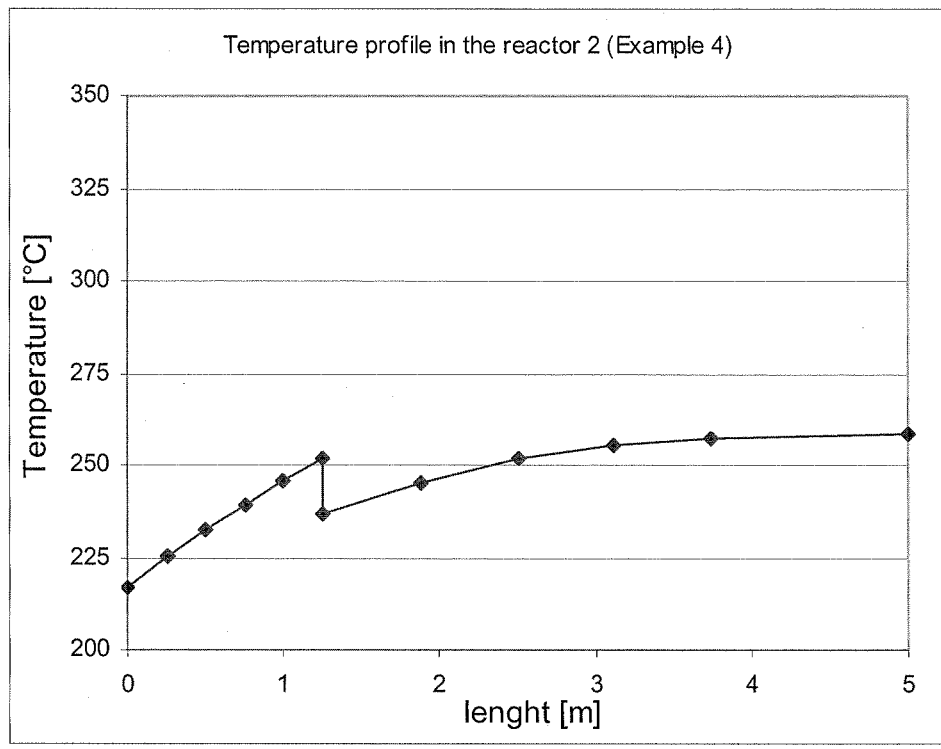
FIG. 7a shows the temperature profile for the reactor 2 in Example 4.
Figure 7B:
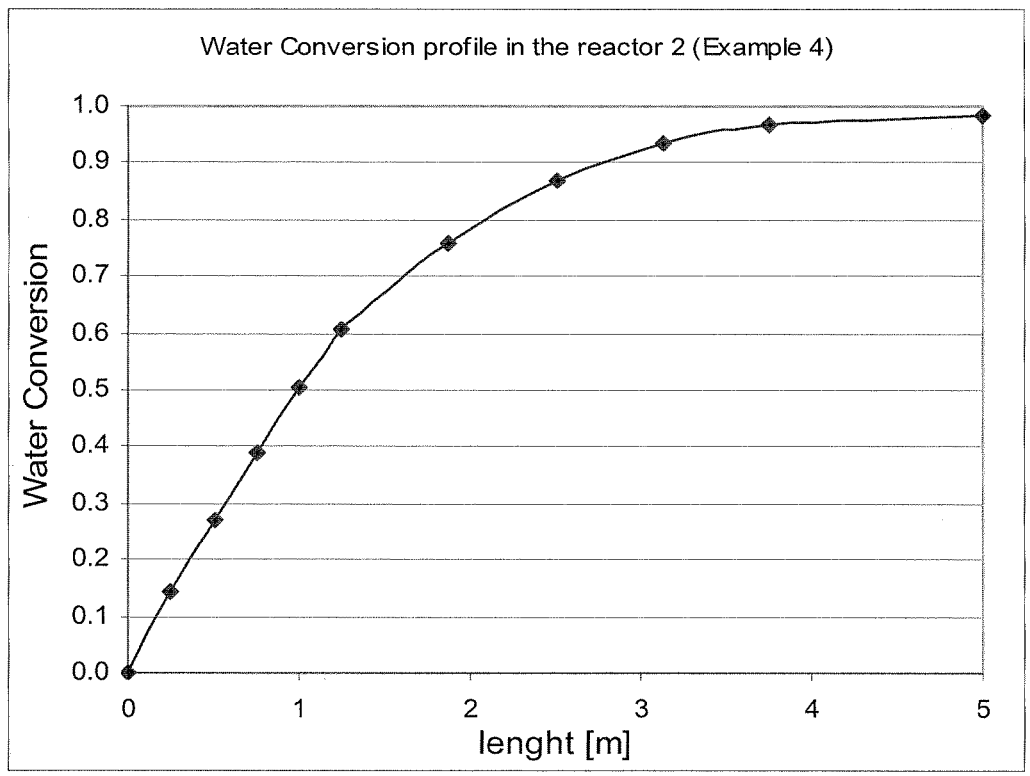
FIG. 7b shows the water conversion profile for the reactor 2 in Example 4.

The gaseous mixture is introduced into a condenser, where water and ethanol are removed. The liquid stream is fed to a heater, where it is vaporized and superheated back to 217° C. and then mixed with 205.2 kmol/hr of pure CO coming from the combustor, such that molar excess of CO is 2. This mixture is introduced into a two-stage adiabatic reactor operating at 5 atmospheres, with cooling between the stages. The adiabatic reactor contains 7600 liters of catalyst. The exit temperature after the first stage is 252° C.; the stream is cooled down to 237° C., and the conversion is finished at the second stage, where the exit temperature is 258° C. FIG. 7a shows the temperature profile for the second reactor. FIG. 7b shows the water conversion profile for the second reactor. The exit conversion ratio is 0.9845, and the exit gas contains 71.24% ethanol, 0.15% water, 9.73% CO, 9.44% $CO_2$ and 9.44% $H_2$. After condensation, the purity of the ethanol after condensation is 99.92 wt %.

EXAMPLE 5

Inventive-Simulation

Water-gas shift reaction in two consecutive cooled tubular reactors with injection of CO between reactors.

A feed of 4574 kmol/hr of a mixture containing 33.34% water, 16.67% ethanol, 33.34% CO, 8.33% $H_2$ and 8.33% $CO_2$ is injected in a tubular non-isothermal non-adiabatic reactor with 6,000 tubular reaction spaces (I.D.=2.54 cm), each 6 m long, operating at 277° C. and 5 atmospheres pressure. See the Table for the amount of total catalysis present. This mixture is produced by mixing the gas produced by the combustion in a furnace of carbon in a stream of oxygen and $CO_2$ with the stream of water and ethanol containing 66 wt % of water from the beer column and 20% of a recycle stream containing 13.0% CO, 43.48% $CO_2$ and 43.48% $H_2$. The reactor is cooled by boiling pressurized water at 58 atm, resulting in the generation of steam.

Figure 8A:
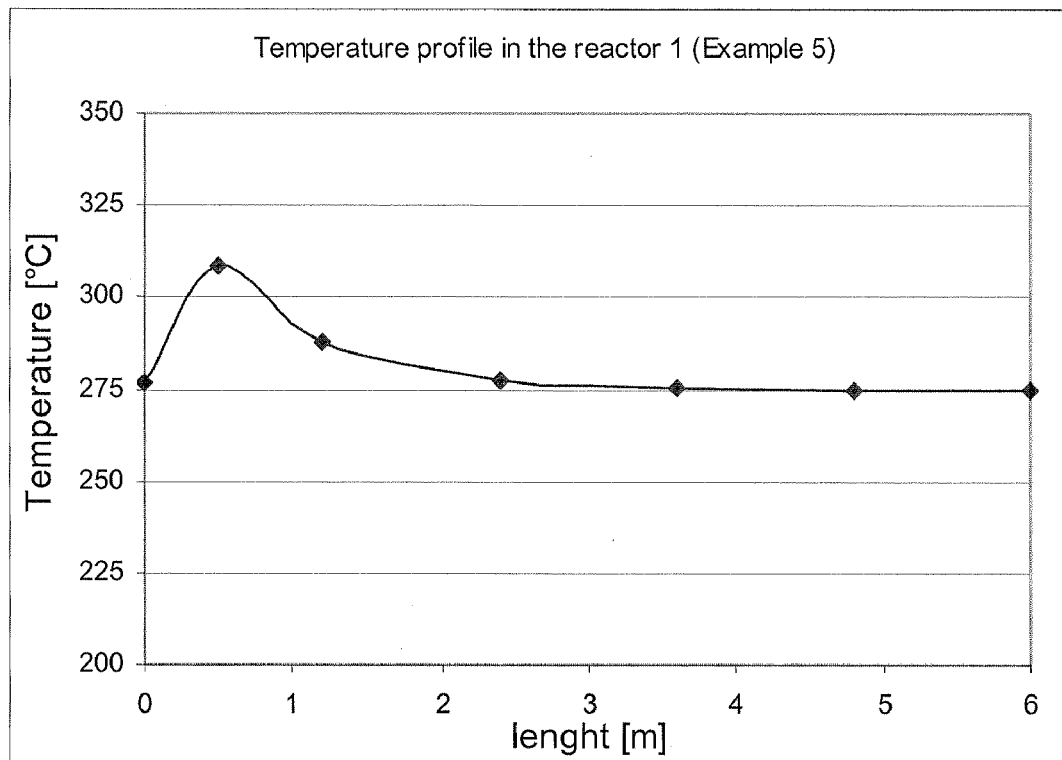
FIG. 8a shows the temperature profile for the reactor 1 in Example 5.
Figure 8B:
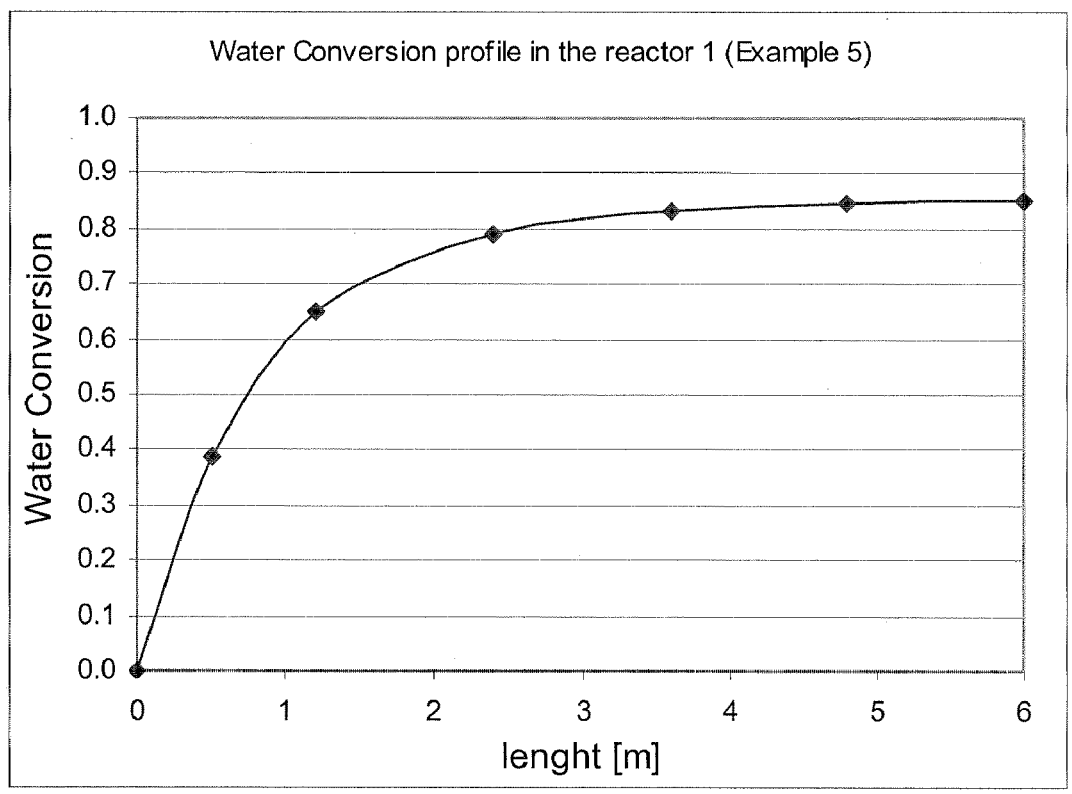
FIG. 8b shows the water conversion profile for the reactor 1 in Example 5.

The reactor has a hot spot of 308.3° C., and the exit conversion is 0.85. FIG. 8a shows the temperature profile for the first non-adiabatic tubular reactor in this example. FIG. 8b shows the water conversion profile for the first reactor. The composition of the exit gas is 16.66% ethanol, 5.00% water, 5.00% CO, 36.66% $CO_2$ and 36.66% $H_2$. The exit gas is cooled, water and alcohol are condensed, and the non-condensable gases CO, $CO_2$ and $H_2$ are removed. The liquid stream containing water and alcohol is evaporated in a heater and mixed with a fresh CO, and the resulting gaseous mixture is injected in a second non-isothermal non-adiabatic tubular reactor. The composition of the feed gas is 48.78% ethanol, 14.65% water and 36.57% CO. The inlet temperature is 217° C., and the pressure is 5 atmospheres.

Figure 9A:
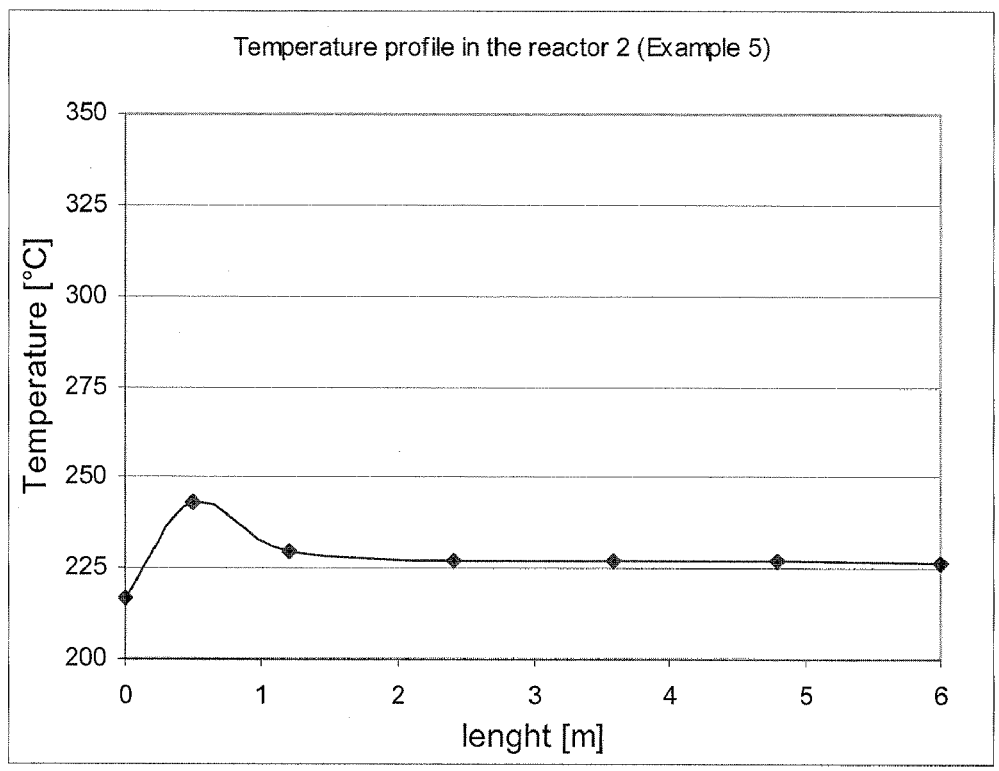
FIG. 9a shows the temperature profile for the reactor 2 in Example 5.
Figure 9B:
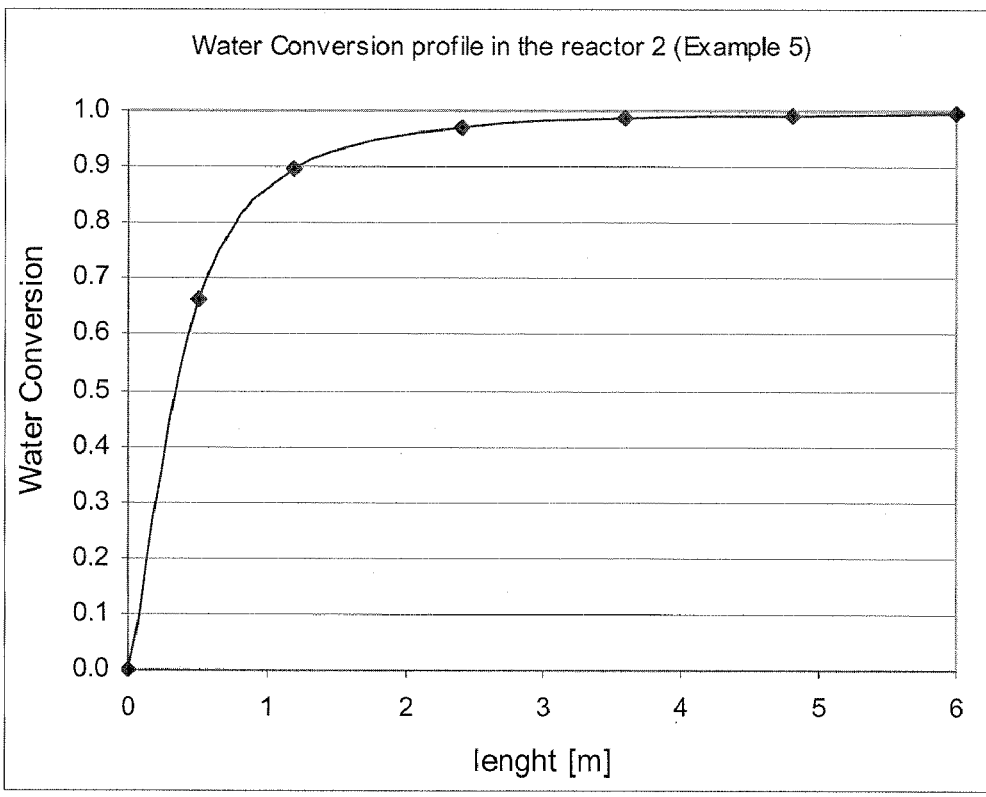
FIG. 9b shows the water conversion profile for the reactor 2 in Example 5.

The hot spot in the reactor reaches a temperature of 243° C., and the lower portion of the reactor operates at isothermal conditions. FIG. 9a shows the temperature profile for the second non-adiabatic reactor. FIG. 9b shows the water conversion profile for the second reactor. The conversion in this reactor is 0.9942, the composition of the exit gas is 48.84% ethanol, 21.90% CO, 14.59% $CO_2$ and 14.59% $H_2$ (molar fractions). This gas is cooled in a condenser, and the purity of the ethanol after condensation is 99.93 wt %.

EXAMPLE 6

Inventive-Simulation

Water-gas shift reaction in two consecutive cooled tubular reactors with injection of CO between reactors and removal of $CO_2$ after the second reactor. This example is a modification of Example 5, wherein the produced $CO_2$ is removed in an absorption column after the gas streams from the first and second reactors are mixed.

A feed of 4195 kmol/hr of a mixture containing 36.35% water, 18.17% ethanol, 36.35% CO, and 9.13% $H_2$ is injected in a tubular non-isothermal non-adiabatic reactor with 6,000 tubes (I.D.=2.54 cm), each 6 m long, operating at 227° C. (inlet) and 5 atmospheres pressure. This mixture is produced by mixing the gas produced by the combustion in a furnace of carbon in a stream of oxygen and $CO_2$ with the stream of water and alcohol containing 66 wt % water from the beer column and 20% of a recycle stream containing 27.04% CO and 72.96% $H_2$. The reactor is cooled by boiling pressurized water at 26 atmospheres, resulting in the generation of steam.

Figure 10A:
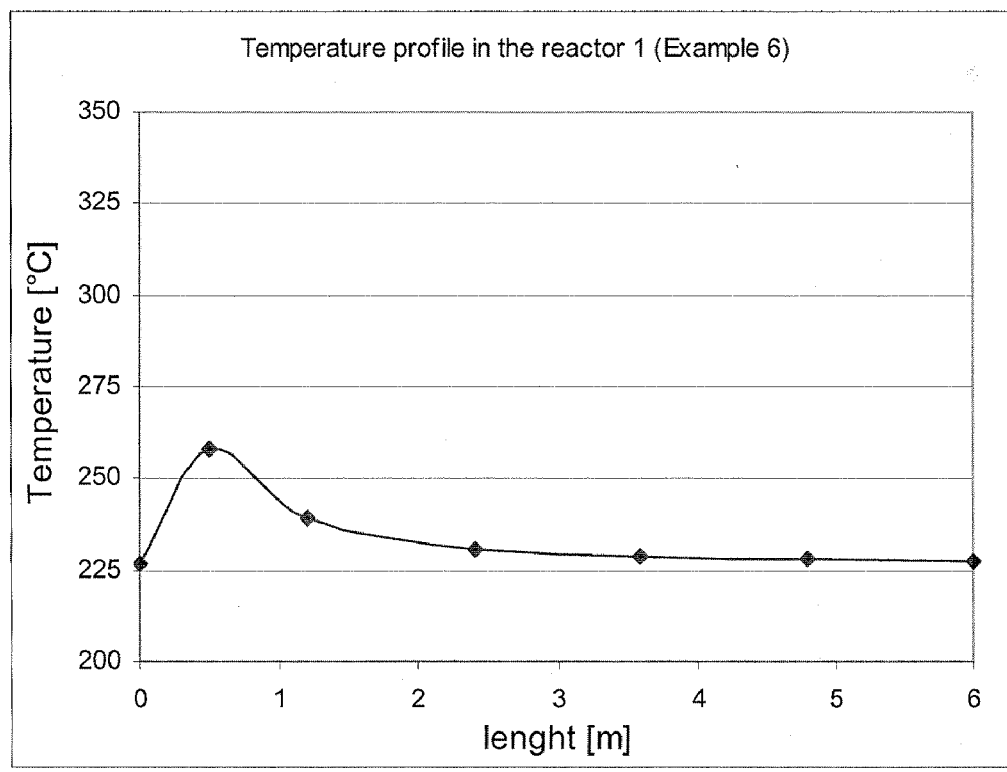
FIG. 10a shows the temperature profile for the reactor 1 in Example 6.
Figure 10B:
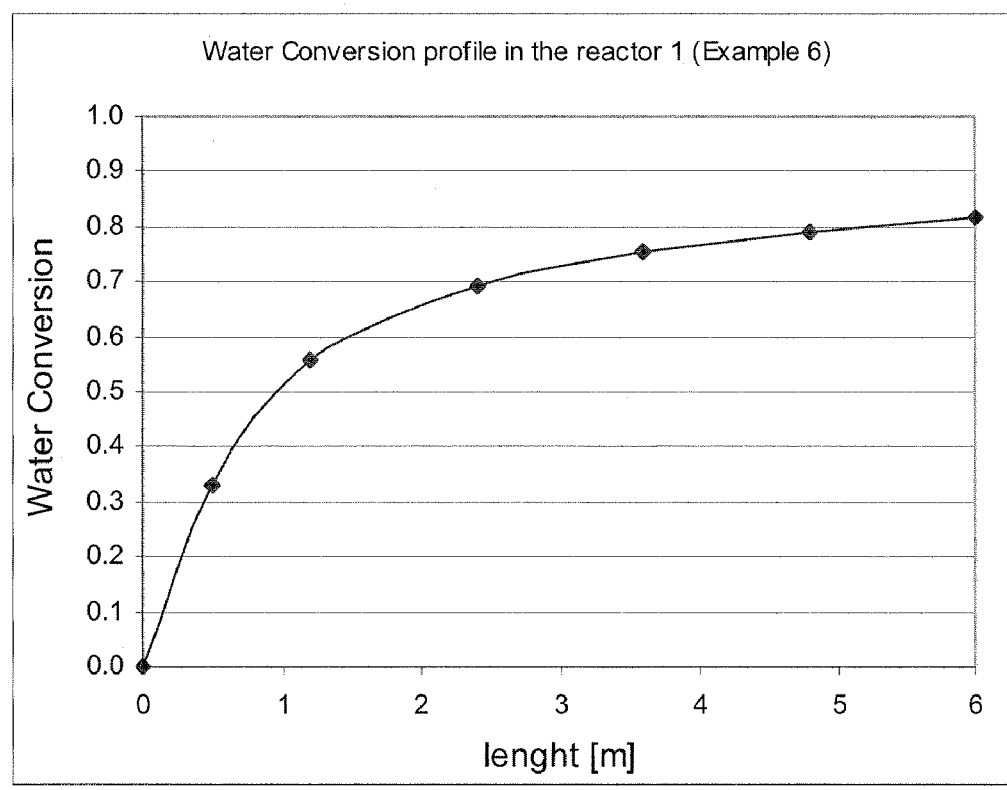
FIG. 10b shows the water conversion profile for the reactor 1 in Example 6.

The reactor has a hot spot of 258° C., and the exit conversion is 0.817. FIG. 10a shows the temperature profile for the first non-adiabatic tubular reactor in this example. FIG. 10b shows the water conversion profile for the first reactor. The composition of the exit gas is 19.16% ethanol, 6.38% water, 6.38% CO, 31.96% $CO_2$ and 36.12% $H_2$. The exit gas is cooled, water and ethanol is condensed and the non-condensable gases CO, $CO_2$ and $H_2$ are removed. The liquid stream containing water and alcohol is evaporated in a heater and mixed with 660 kmol/hr of fresh CO, and the resulting gaseous mixture is injected in a second non-isothermal non-adiabatic tubular reactor with 5,000 tubes, each 6 m long. The inlet temperature is 217° C., and the pressure is 5 atmospheres.

Figure 11A:
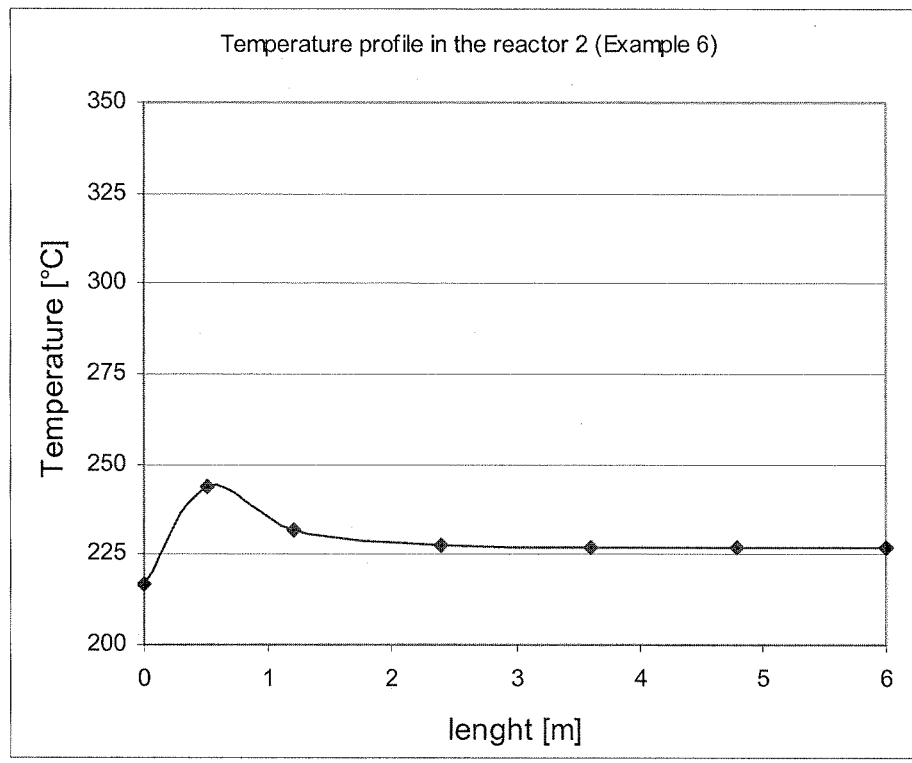
FIG. 11a shows the temperature profile for the reactor 2 in Example 6.
Figure 11B:
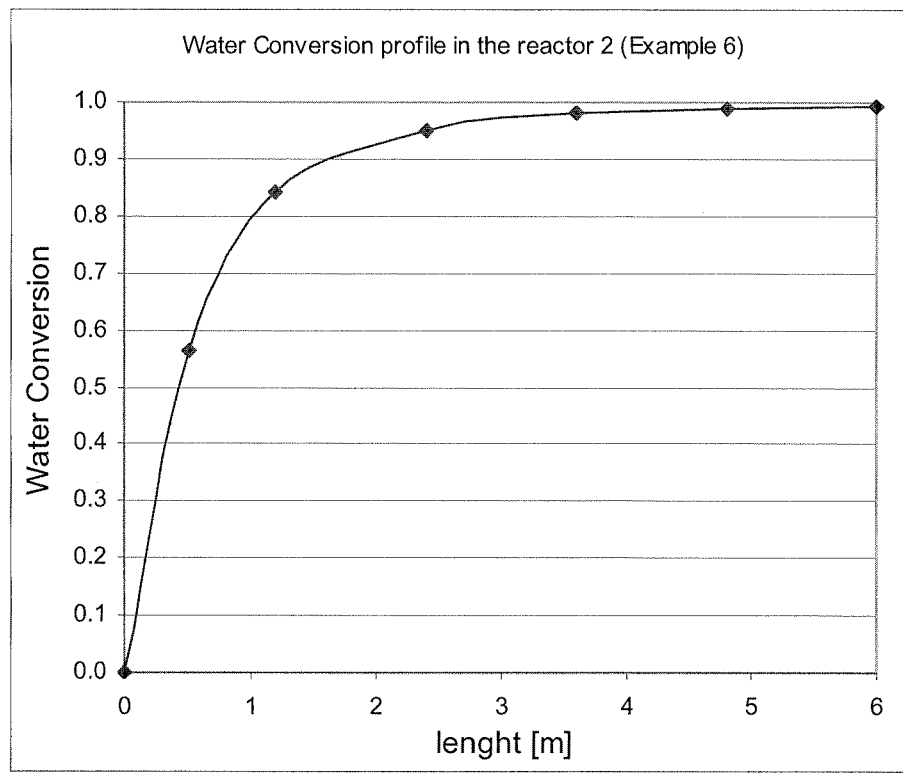
FIG. 11b shows the water conversion profile for the reactor 2 in Example 6.

The hot spot in the reactor reaches a temperature of 243.8° C. and the lower portion of the reactor operates at isothermal conditions. FIG. 11a shows the temperature profile for the second non-adiabatic reactor and FIG. 11b shows the water conversion profile. The conversion in this reactor is 0.9926, and the composition of the exit gas is 46.49% ethanol, 0.11% water, 22.67% CO, 15.36% $CO_2$ and 15.36% $H_2$ (molar fractions). This gas is cooled in a condenser, and the purity of the ethanol after condensation is 99.90 wt %.

EXAMPLE 7

Inventive-Simulation

Water-gas shift reaction in two consecutive cooled tubular reactors with injection of CO between reactors. Reactors are operated at higher pressure.

This system is a modification of the system described in Example 5. A feed of 8368 kmol/hr of a mixture containing 18.22% water, 9.11% ethanol, 18.22% CO, 27.22% $H_2$ and 27.22% $CO_2$ is injected in a tubular non-isothermal non-adiabatic reactor with 5,000 tubes (I.D.=2.54 cm), each 5 m long, operating at 227° C. (inlet) and 15 atmospheres pressure. This mixture is produced by mixing the gas produced by the combustion in a furnace of carbon in a stream of oxygen and $CO_2$ with the stream of water and alcohol containing 66 wt % water from the beer column and 60% of a recycle stream containing 12.13% CO, 43.94% $CO_2$ and 43.94% $H_2$. The reactor is cooled by boiling water pressurized to 26 atmospheres, resulting in the generation of steam.

Figure 12A:
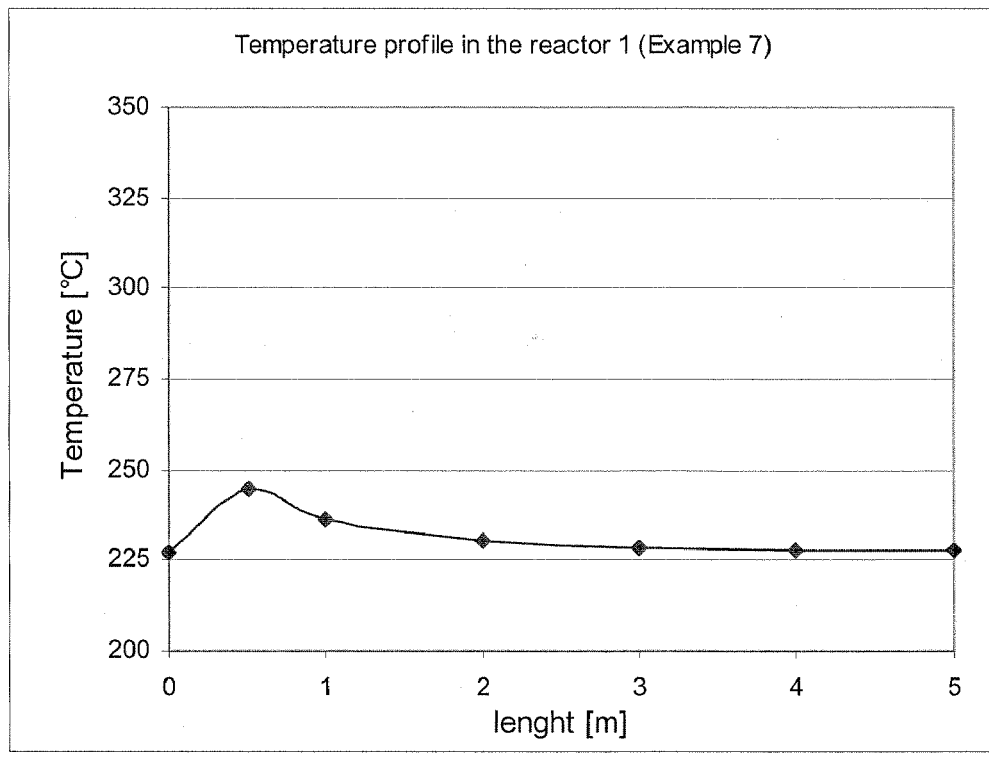
FIG. 12a shows the temperature profile for the reactor 1 in Example 7.
Figure 12B:
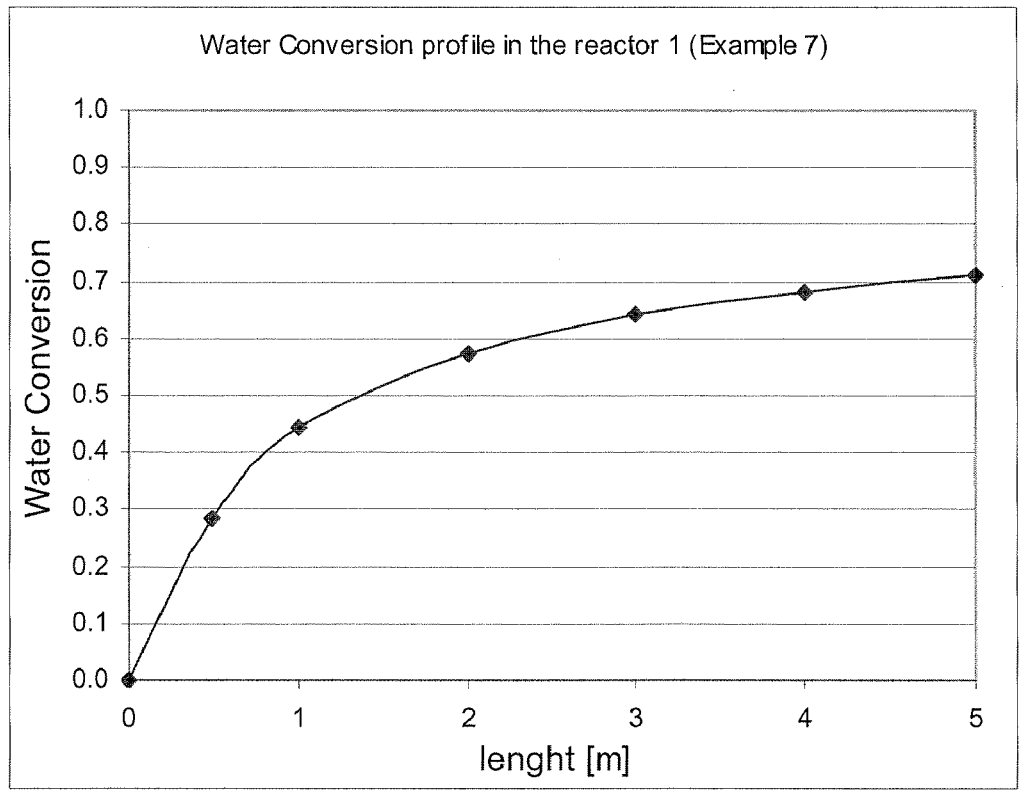
FIG. 12b shows the water conversion profile for the reactor 1 in Example 7.

The reactor has a hot spot of 245° C., and the exit conversion is 0.711. FIG. 12a shows the temperature profile for the first non-adiabatic tubular reactor in this example. FIG. 12b shows the water conversion profile for the first reactor. The composition of the exit gas is 9.19% ethanol, 5.31% water, 4.85% CO, 40.08% $CO_2$ and 40.08% $H_2$. The exit gas is cooled, water and alcohol are condensed, and the non-condensable gases CO, $CO_2$ and $H_2$ are removed. The liquid stream containing water and alcohol is evaporated in a heater and mixed with 1048 kmol/hr of fresh CO, and the resulting gaseous mixture is injected into a second non-isothermal non-adiabatic tubular reactor with 2,000 tubes (I.D.=2.54 cm), each 4 m long. The composition of the feed gas is 34.01% ethanol, 19.65% water and 46.34% CO. The inlet temperature is 217° C., and the pressure is 9 atmospheres.

Figure 13A:
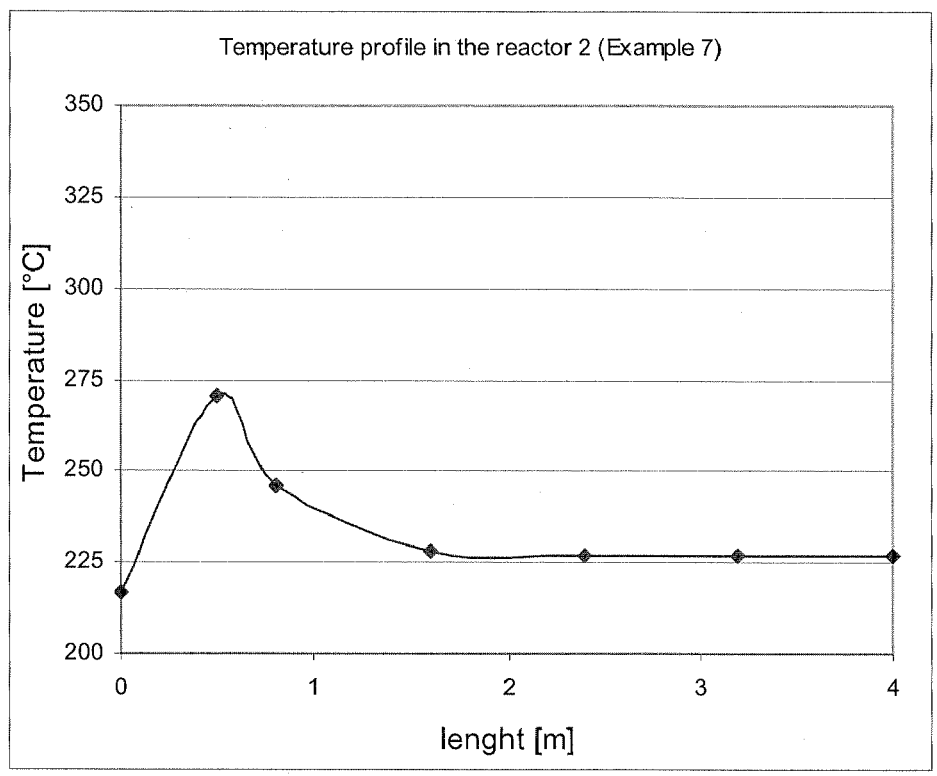
FIG. 13a shows the temperature profile for the reactor 2 in Example 7.
Figure 13B:
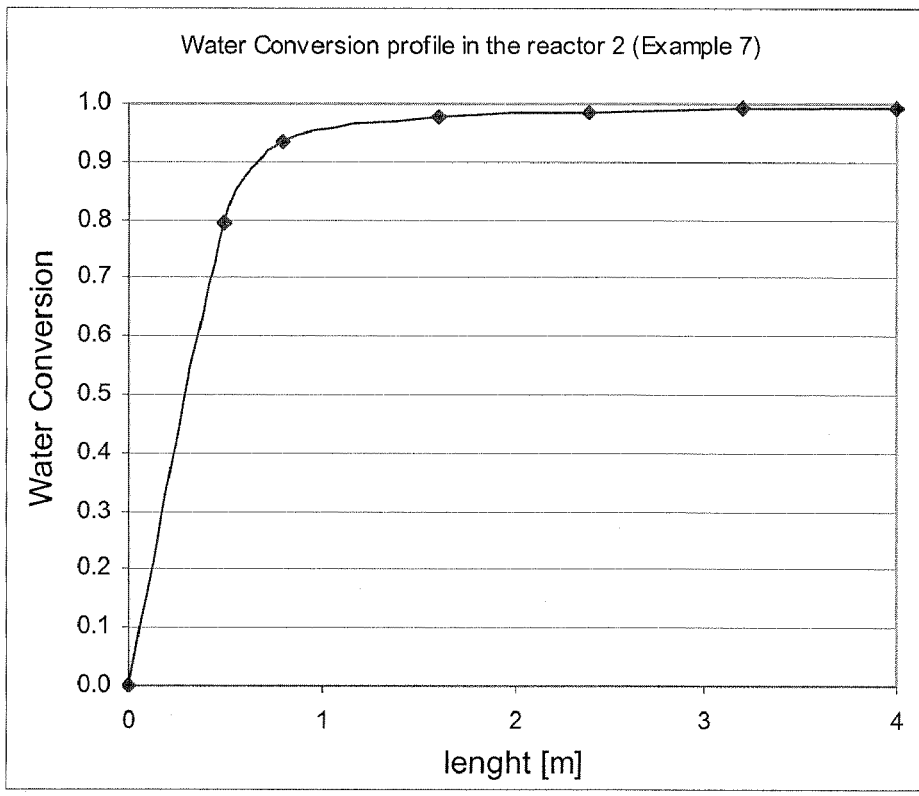
FIG. 13b shows the water conversion profile for the reactor 2 in Example 7.

The hot spot in the reactor reaches 270° C., and the lower portion of the reactor operates at isothermal conditions. The conversion in this reactor is 0.9924, and the composition of the exit gas is 34.08% ethanol, 0.15% water, 26.69 mol % CO, 19.54% $CO_2$ and 19.54% $H_2$. FIG. 13a shows the temperature profile for the second non-adiabatic reactor and FIG. 13b shows the water conversion profile. This gas is cooled in a condenser, and the purity of the ethanol after condensation is 99.83 wt %.

TABLE 1

Summary of results for examples 3-7

| Example | Carbon input kg/hr (tons/hr) | Catalyst needed kg (tons) | Product purity wt % | Comments[1] |
|---|---|---|---|---|
| 3 | 19,141 (21.1) | 34,473 (38) | 99.72 | BC overhead vapor, 66% water content Reactor 1 = non-adiabatic, 5 atm Reactor 2 = adiabatic, 4 atm |

TABLE 1-continued

Summary of results for examples 3-7

| Example | Carbon input kg/hr (tons/hr) | Catalyst needed kg (tons) | Product purity wt % | Comments[1] |
|---|---|---|---|---|
| 4 | 17,145 (18.9) | 34,473 (38) | 99.92 | BC overhead vapor, 47% water content<br>Reactor 1 = non-adiabatic, 5 atm<br>Reactor 2 = adiabatic, 5 atm |
| 5 | 18,234 (20.1) | 45,359 (50) | 99.93 | BC overhead vapor, 66% water content<br>Reactor 1 = non-adiabatic, 5 atm<br>Reactor 2 = non-adiabatic, 5 atm |
| 6 | 18,778 (20.7) | 45,359 (50) | 99.90 | BC overhead vapor, 66% water content<br>$CO_2$ absorption<br>Reactor 1 = non-adiabatic, 5 atm<br>Reactor 2 = non-adiabatic, 5 atm |
| 7 | 17,780 (19.6) | 22,679 (25) | 99.83 | BC overhead vapor, 66% water content<br>Reactor 1 = non-adiabatic, 15 atm<br>Reactor 2 = non-adiabatic, 9 atm |

[1]BC refers to feedstock from a beer column and the percent water content is listed. Reactor 1 is non-adiabatic and is operated at the pressure listed. Reactor 2 is either adiabatic or non-adiabatic as noted and is operated at the pressure listed.

Examples 3-7 represent examples of the overall balance for a two reactor process for producing 100 MMgy (millions of gallons per year) of ethanol. To keep the examples simple, we've assumed that the first reactor has only one stage and the second reactor is divided in two stages. However, reactors may have multiple stages in order to achieve desired conversion. The density of the catalyst is assumed to be 1500 kg/m$^3$. Results are summarized in the TABLE 1.

The above examples illustrate that the inventive process effectively produces dry alcohol from a feedstock that includes a mixture of alcohol and water. The examples also illustrate that a multistage reactor is often advantageous. As can be seen from the examples above, the first stage of the reactor often does not produce alcohol that is sufficiently dry. Embodiments of the invention may provide reduced cost, higher productivity, improved quality, and ease of manufacture.

While the invention has been described by reference to various specific embodiments, it should be understood that numerous changes may be made within the spirit and scope of the inventive concepts described. Accordingly, it should be recognized that the invention is not limited to the described embodiments but has full scope defined by the language of the following claims.

What is claimed:

1. A process for producing dry alcohol comprising the step of contacting a gaseous feedstock, consisting essentially of alcohol and water, with carbon monoxide in the presence of a water-gas shift catalyst at a temperature sufficiently high so that carbon monoxide and water are at least partially consumed and carbon dioxide and hydrogen are formed, thereby removing a portion of said water from said gaseous feedstock to produce said dry alcohol consisting essentially of a mixture of alcohol and residual water.

2. The process according to claim 1 wherein the alcohol comprises ethanol.

3. The process according to claim 1 wherein said dry alcohol comprises about 0.3 wt. % or less of water.

4. The process according to claim 1 wherein methanol is formed.

5. The process according to claim 1 wherein said gaseous feedstock comprises a product of a fermentation process.

6. The process according to claim 5 wherein said fermentation process comprises the fermentation of corn.

7. The process according to claim 1 wherein said gaseous feedstock comprises ethanol produced by hydrating ethylene.

8. The process according to claim 1 wherein said temperature is below the temperature at which significant degradation of the alcohol occurs.

9. The process according to claim 1 wherein said temperature is in the range of about 180° C. to about 350° C.

10. The process according to claim 1 wherein said temperature is in the range of about 200° C. to about 275° C.

11. The process according to claim 1 including the further step of operating said process at a pressure sufficient for good recovery of said dry alcohol.

12. The process according to claim 1 wherein said water-gas shift catalyst comprises a low-temperature catalyst.

13. The process according to claim 1 wherein said water-gas shift catalyst comprises iron, chromium, copper, zinc, or aluminum.

14. The process according to claim 1 wherein said water-gas shift catalyst comprises a copper oxide-zinc oxide catalyst.

15. The process according to claim 1 wherein heat is produced, said process further comprising the step of removing at least a portion of said heat by use of a heat exchanger.

16. The process according to claim 1 wherein heat is produced, said process further comprising the step of removing at least a portion of said heat by converting cooling water to steam.

17. The process according to claim 1 wherein heat is produced, said process further comprising the step of removing a portion of said heat by vaporizing liquid alcohol that is being dried.

18. The process according to claim 1 wherein said alcohol comprises ethanol and wherein heat is produced, said process further comprising the step of removing a portion of said heat by injecting liquid ethanol that is being dried into said mixture and thereby vaporizing said liquid ethanol.

19. The process according to claim 1 wherein said step of producing said mixture comprises a first stage, and further comprising a second stage comprising the step of contacting said mixture with carbon monoxide in the presence of a second water-gas shift catalyst at a temperature sufficiently high so that carbon monoxide and residual water are at least partially consumed and carbon dioxide and hydrogen are formed, thereby removing a portion of said residual water from said mixture and producing a second mixture comprising alcohol and any unconsumed water.

20. The process according to claim 19 wherein heat is produced in said first stage, said process further comprising the step of removing at least a portion of said heat between said stages by converting cooling water to high-pressure steam.

21. The process according to claim 19 wherein heat is produced in said first stage, said process further comprising the step of removing at least a portion of said heat between said stages by injecting liquid alcohol that is being dried into said mixture and thereby vaporizing said liquid alcohol.

22. The process according to claim 19 wherein at least one stage is adiabatic and at least one stage is non-adiabatic.

23. The process according to claim 19 wherein at least one stage comprises one or more tubular reactors.

24. The process according to claim 23 wherein heat is produced by said tubular reactors and further including the step of removing at least a portion of said heat by passing cooling water adjacent to said reactors and converting said cooling water to high-pressure steam.

25. The process according to claim 19 further comprising the step of injecting carbon monoxide into said mixture after said first stage and before said second stage.

26. The process according to claim 19 wherein said second stage has an operating temperature of about 180° C. to about 250° C.

27. The process according to claim 19 wherein said stages have an operating pressure of about 1 atmosphere to about 20 atmospheres.

28. The process according to claim 19 wherein said stages have an operating pressure of about 3 atmospheres to about 20 atmospheres.

29. The process according to claim 19 wherein said stages have an operating pressure of about 10 atmospheres to about 15 atmospheres.

30. A process for producing dry alcohol comprising the steps of: a) contacting a gaseous feedstock, consisting essentially of alcohol and water, with carbon monoxide in the presence of a water-gas shift catalyst at a temperature sufficiently high so that carbon monoxide and water are at least partially consumed and carbon dioxide, hydrogen, and heat are produced, thereby removing a portion of said water; b) recovering the dry alcohol and c) utilizing said heat to produce high-pressure steam.

31. The process according to claim 30 wherein a portion of said high-pressure steam is used to heat feedstock thereby forming said gaseous feedstock.

32. The process according to claim 30 wherein a portion of said high-pressure steam is used to generate electricity.

33. The process according to claim 30 wherein said process occurs in a production plant and wherein said high-pressure steam is used in the operation of said production plant.

34. The process according to claim 30 wherein methanol is formed.

35. A low-pressure process for producing methanol in the presence of alcohol to produce a dried alcohol stream comprising the step of contacting a gaseous feedstock, consisting essentially of alcohol and water, with carbon monoxide in the presence of a water-gas shift catalyst at a temperature sufficiently high so that carbon monoxide and water are at least partially consumed and carbon dioxide and hydrogen are formed, and at a pressure below about 40 atmospheres, and thereby forming said methanol in the presence of alcohol to produce a dried alcohol stream.

36. The process according to claim 35 wherein said pressure is about 20 atmospheres or less.

37. The process according to claim 35 wherein said pressure is about 10 atmospheres to about 15 atmospheres.

\* \* \* \* \*